(12) United States Patent
Harada et al.

(10) Patent No.: US 7,666,967 B2
(45) Date of Patent: Feb. 23, 2010

(54) ESTER COMPOUND, POLYMER, RESIST COMPOSITION, AND PATTERNING PROCESS

(75) Inventors: Yuji Harada, Joetsu (JP); Jun Hatakeyama, Joetsu (JP); Yoshio Kawai, Joetsu (JP); Masaru Sasago, Osaka (JP); Masayuki Endo, Osaka (JP); Kazuhiko Maeda, Tokyo (JP); Haruhiko Komoriya, Kawagoe (JP); Michitaka Ootani, Kawagoe (JP)

(73) Assignees: Shin-Etsu Chemical Co., Ltd., Tokyo (JP); Panasonic Corporation, Kadoma-Shi (JP); Central Glass Co., Ltd., Ube-Shi (JP)

(*) Notice: Subject to any disclaimer, the term of this patent is extended or adjusted under 35 U.S.C. 154(b) by 233 days.

(21) Appl. No.: 11/606,069

(22) Filed: Nov. 30, 2006

(65) Prior Publication Data
US 2007/0128555 A1    Jun. 7, 2007

(30) Foreign Application Priority Data
Dec. 2, 2005   (JP) .............................. 2005-349110

(51) Int. Cl.
   *C08F 214/18*   (2006.01)
(52) U.S. Cl. ............. 526/329.4; 526/321; 526/328.5; 430/313; 524/556
(58) Field of Classification Search ................. 524/556; 216/103
   See application file for complete search history.

(56) References Cited

U.S. PATENT DOCUMENTS

| | | | |
|---|---|---|---|
| 4,491,628 A | 1/1985 | Ito et al. | |
| 5,310,619 A | 5/1994 | Crivello et al. | |
| 6,200,725 B1 | 3/2001 | Takechi et al. | |
| 6,280,898 B1* | 8/2001 | Hasegawa et al. | 430/270.1 |
| 6,329,125 B2 | 12/2001 | Takechi et al. | |
| 6,710,148 B2* | 3/2004 | Harada et al. | 526/245 |
| 2001/0026901 A1 | 10/2001 | Maeda et al. | |
| 2005/0186501 A1* | 8/2005 | Kishimura et al. | 430/270.1 |
| 2005/0221221 A1* | 10/2005 | Hatakeyama et al. | 430/270.1 |
| 2005/0227174 A1* | 10/2005 | Hatakeyama et al. | 430/270.1 |
| 2005/0233254 A1* | 10/2005 | Hatakeyama et al. | 430/311 |

FOREIGN PATENT DOCUMENTS

| | | |
|---|---|---|
| JP | 63-27829 A | 2/1988 |
| JP | 2-27660 B2 | 6/1990 |
| JP | 9-73173 A | 3/1997 |
| JP | 9-90637 A | 4/1997 |
| JP | 9-230595 A | 9/1997 |
| JP | 10-10739 A | 1/1998 |
| JP | 2000-26446 A | 1/2000 |
| JP | 2000-159758 A | 6/2000 |
| WO | WO-97/33198 A1 | 9/1997 |

OTHER PUBLICATIONS

Chiba et al. Journal of Photopolymer Science and Technology, 13 (4), 2000, 657-664.*
Hiroshi Ito, Adv. Polym. Sci., (2005), 172, pp. 37 and 114.*
Proc. SPIE, vol. 4690, xxix-xxxiii.
Proc. SPIE, vol. 5040, pp. 724, (2003).
Proc. SPIE, vol. 4345, pp. 273, (2001).

* cited by examiner

*Primary Examiner*—David Wu
*Assistant Examiner*—Vu Nguyen
(74) *Attorney, Agent, or Firm*—Birch, Stewart, Kolasch & Birch, LLP

(57) ABSTRACT

A polymer comprising recurring units (2) obtained through polymerization of an ester compound of formula (1) is used to form a resist composition. $R^1$ is F or $C_1$-$C_6$ fluoroalkyl, $R^2$ is H or $C_1$-$C_8$ alkyl, $R^3$ is O or $C_1$-$C_6$ alkylene, $R^4$ and $R^5$ each are H or $C_1$-$C_{10}$ alkyl or fluoroalkyl, and $R^6$ is H or an acid labile group. The resist composition, when processed by ArF lithography, has advantages including improved resolution, transparency, minimal line edge roughness, and etch resistance. The resist composition exhibits better performance when processed by ArF immersion lithography with liquid interposed between a projection lens and a wafer.

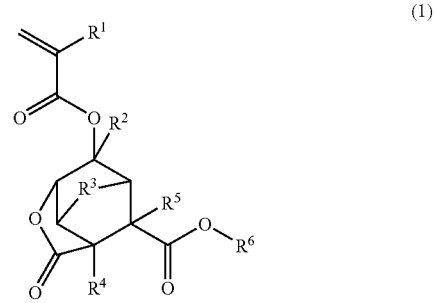

(1)

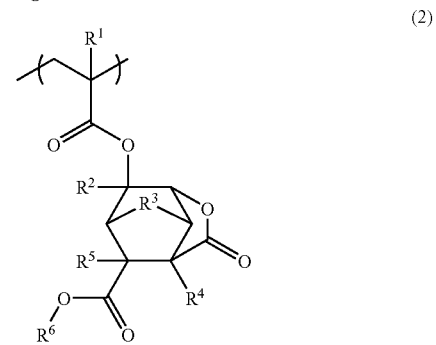

(2)

4 Claims, No Drawings

ESTER COMPOUND, POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2005-349110 filed in Japan on Dec. 2, 2005, the entire contents of which are hereby incorporated by reference.

TECHNICAL FIELD

This invention generally relates to chemically amplified positive resist compositions for use in the lithography technology for the microfabrication of semiconductor devices or the like, especially the immersion photolithography utilizing water interposed between a projection lens and a wafer. More particularly, it relates to ester compounds which are useful as monomers to form base polymers for use in such resist compositions, resist compositions, and a patterning process.

BACKGROUND ART

In the recent drive for higher integration and operating speeds in LSI devices, the pattern rule is made drastically finer. The rapid advance toward finer pattern rules is grounded, in part, on the development of a light source of a shorter wavelength. A wavelength reduction from a mercury lamp of i-line (365 nm) to a KrF excimer laser (248 nm) enabled the mass production process of 64 M-bit dynamic random access memory (DRAM, processing feature size 0.25 μm or less). For the fabrication of DRAM with a degree of integration of 256 M and 1 G or more, photolithography using ArF excimer laser light (193 nm) has been under active investigation. The ArF lithography combined with a lens having an increased numerical aperture (NA) of 0.9 or greater is considered to comply with 65-nm node devices. For the fabrication of next 45-nm node devices, a $F_2$ laser of 157 nm wavelength became a candidate. However, for the reasons that the scanner becomes expensive, the optical system must be altered, and the etch resistance of resist is low; the application of $F_2$ lithography was postponed. The ArF immersion lithography was proposed as a replacement. Since then, efforts have been made for the early introduction thereof (see Proc. SPIE Vol. 4690 xxix).

In the ArF immersion lithography, the space between the projection lens and the wafer is filled with water, and ArF excimer laser radiation is irradiated through the water. Since water has a refractive index of 1.44 at 193 nm, pattern formation is possible even using a lens with NA of 1.0 or greater. Theoretically, it is possible to increase the NA to 1.44. The resolution is improved by an increment of NA. A combination of a lens having NA of at least 1.2 with ultra-high resolution technology suggests a way to the 45-nm node (see Proc. SPIE, Vol. 5040, p 724, 2003).

In the ArF lithography, acid-catalyzed chemical amplification positive working resist materials are used as disclosed in U.S. Pat. No. 4,491,628 and U.S. Pat. No. 5,310,619 (JP-B 2-27660 and JP-A 63-27829). While novolac resins and polyhydroxystyrene resins are used as the alkali-soluble base resin in the i-line and KrF lithography resists, they cannot be used in the ArF lithography because of their very strong absorption at a wavelength around 193 nm. Instead, studies were made on poly(meth)acrylate resins and resins comprising cycloaliphatic olefin such as norbornene as polymerized units, both using carboxyl groups as the alkali-soluble group (see JP-A 9-73173, JP-A 10-10739, JP-A 9-230595 and WO 97/33198).

Of these, the poly(meth)acrylate resins are expected to reach a practical level because of easy polymerization. One of the poly(meth)acrylate resins proposed thus far is a poly(meth)acrylate resin having methyladamantyl groups as the acid labile group and lactone rings as the adhesive group as disclosed in JP-A 9-90637. Resins containing norbornyl lactone as the adhesive group were developed for enhancing etch resistance as disclosed in JP-A 2000-26446 and JP-A 2000-159758. A study is made to apply to the ArF lithography a copolymer of norbornene and a-trifluoromethylacrylate, which was the base polymer candidate for $F_2$ resist, because it has high transparency around wavelength 193 nm and high etching resistance (see Proc. SPIE, Vol. 4345, p 273 (2001), for example).

Since the ArF immersion lithography carries out light exposure through water, there arise problems different from the conventional lithography. For example, if water left on the resist film after exposure penetrates into the resist film, it, even in trace amounts, can cause development defects. One of means proposed thus far for preventing water penetration is by forming a topcoat film on the resist film. Another effective means contemplated is by enhancing the water repellency of the resist film itself.

In order to enhance the water repellency of the resist film, the base resin must be rendered more water repellent. In general, resins can be made more water repellent by incorporating fluorine atoms. However, as the proportion of fluorine incorporated is increased, the resins becomes less adherent to substrates. It would be desirable to have a fluorinated resin which has high water repellency while maintaining good substrate adhesion.

SUMMARY OF THE INVENTION

An object of the invention is to provide a resist composition which allows for effective immersion lithography, a base polymer therefor, a monomer compound useful as the raw material for the polymer, and a patterning process using the resist composition.

The inventors have found that a polymerizable ester compound containing a fluorinated alkyl group, a lactone ring, and an acid-eliminatable unit within a common molecule can be polymerized into a polymer which meets water repellency as needed for the immersion lithography and is improved in resin transparency, dry etching resistance, and resist film resolution.

Accordingly, the present invention provides an ester compound, a polymer, a resist composition, and a patterning process, as defined below.

In one aspect, the invention provides an ester compound having the general formula (1).

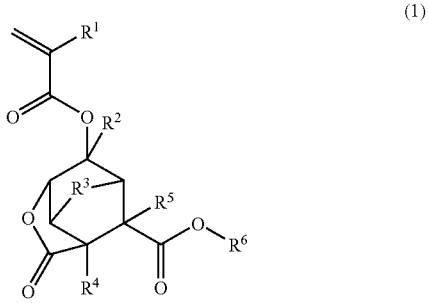

Herein $R^1$ is a fluorine atom or a straight or branched fluorinated alkyl group of 1 to 6 carbon atoms, $R^2$ is a hydrogen atom or a straight, branched or cyclic alkyl group of 1 to 8 carbon atoms, $R^3$ is an oxygen atom or a straight, branched or cyclic alkylene group of 1 to 6 carbon atoms, $R^4$ and $R^5$ each are a hydrogen atom or a straight, branched or cyclic alkyl or fluorinated alkyl group of 1 to 10 carbon atoms, and $R^6$ is a hydrogen atom or an acid labile group. Most preferably, $R^1$ in formula (1) is trifluoromethyl.

In another aspect, the invention provides a polymer comprising recurring units having the general formula (2), the polymer having a weight average molecular weight of 1,000 to 500,000.

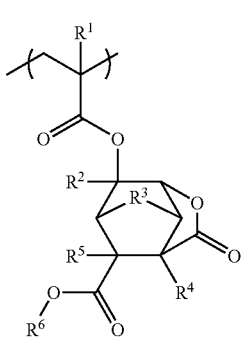

(2)

Herein $R^1$ is a fluorine atom or a straight or branched fluorinated alkyl group of 1 to 6 carbon atoms, $R^2$ is a hydrogen atom or a straight, branched or cyclic alkyl group of 1 to 8 carbon atoms, $R^3$ is an oxygen atom or a straight, branched or cyclic alkylene group of 1 to 6 carbon atoms, $R^4$ and $R^5$ each are a hydrogen atom or a straight, branched or cyclic alkyl or fluorinated alkyl group of 1 to 10 carbon atoms, and $R^6$ is a hydrogen atom or an acid labile group.

A preferred embodiment is a polymer comprising recurring units having the general formula (2) and recurring units having the general formula (3), the polymer having a weight average molecular weight of 1,000 to 500,000,

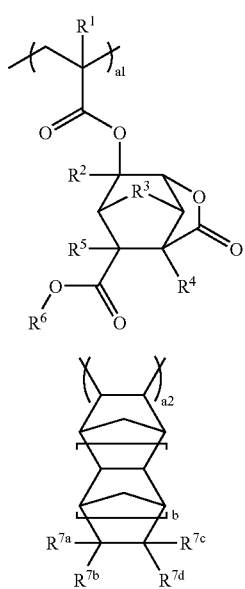

(2)

(3)

Herein $R^1$ to $R^6$ are as defined above, $R^{7a}$, $R^{7b}$, $R^{7c}$, and $R^{7d}$ each are a hydrogen atom, fluorine atom, straight, branched or cyclic alkyl or fluorinated alkyl group of 1 to 10 carbon atoms, $-R^8-C(=O)-OR^9$, or $-R^8-OR^9$, $R^8$ is a single bond or a straight, branched or cyclic alkylene or fluorinated alkylene group of 1 to 10 carbon atoms, $R^9$ is a hydrogen atom or an acid labile group, the subscripts a1 and a2 are $0<a1<1$, $0<a2<1$, and $0<a1+a2\leq1$. Most preferably, $R^1$ in formula (2) is trifluoromethyl.

In a further aspect, the invention provides a resist composition comprising the polymer defined above; specifically a chemically amplified positive resist composition comprising (A) the polymer defined above, (B) an organic solvent, (C) a photoacid generator, and optionally (D) a basic compound and (E) a dissolution inhibitor.

In a still further aspect, the invention provides:

a process for forming a pattern, comprising the steps of (1) applying the resist composition defined above onto a substrate to form a coating, (2) heat treating the coating and exposing it to high-energy radiation in a wavelength band of 100 to 250 nm or 1 to 30 nm through a photomask, and (3) optionally heat treating and developing the exposed coating with a developer;

a process for forming a pattern, comprising the steps of (1) applying the resist composition defined above onto a substrate to form a resist coating, (2) heat treating the resist coating, placing a liquid between the substrate and a projection lens, and exposing the resist coating to high-energy radiation in a wavelength band of 100 to 250 nm through a photomask, and (3) optionally heat treating and developing the resist coating with a developer; or a process for forming a pattern, comprising the steps of (1) applying the resist composition defined above onto a substrate to form a resist coating, (2) heat treating the resist coating and applying a protective coating material thereto, (3) heat treating, placing a liquid between the substrate and a projection lens, and exposing the resist coating to high-energy radiation in a wavelength band of 100 to 250 nm through a photomask, (4) optionally heat treating and stripping the protective coating, and (5) developing the resist coating with a developer.

The high-energy radiation is typically an ArF excimer laser, $F_2$ laser, or $Ar_2$ laser.

BENEFITS OF THE INVENTION

The ester compound of the invention can be polymerized into a polymer which is used as a base resin to formulate a resist composition. The resist composition, when processed by the lithography involving ArF exposure, has many advantages including improved resolution and transparency, minimal line edge roughness, improved etch resistance, and especially minimal surface roughness after etching. Since the resin is fully repellent to water, the resist composition exhibits similar better performance when processed by the ArF immersion lithography with liquid interposed between the projection lens and the wafer.

DESCRIPTION OF THE PREFERRED EMBODIMENTS

The terms "a" and "an" herein do not denote a limitation of quantity, but rather denote the presence of at least one of the referenced item.

As used herein, the notation $(C_n-C_m)$ means a group containing from n to m carbon atoms per group.

Ester Compound

The polymerizable ester compounds of the invention have the general formula (1).

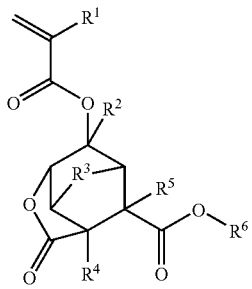
(1)

Herein $R^1$ is a fluorine atom or a straight or branched fluorinated alkyl group of 1 to 6 carbon atoms, $R^2$ is a hydrogen atom or a straight, branched or cyclic alkyl group of 1 to 8 carbon atoms, $R^3$ is an oxygen atom or a straight, branched or cyclic alkylene group of 1 to 6 carbon atoms, $R^4$ and $R^5$ each are a hydrogen atom or a straight, branched or cyclic alkyl or fluorinated alkyl group of 1 to 10 carbon atoms, and $R^6$ is a hydrogen atom or an acid labile group.

For the compound of formula (1), there can exist enantiomers and diastereomers resulting from asymmetric carbon and cyclic structure. Formula (1) collectively represents all such stereoisomers. Such stereoisomers may be included alone or in admixture.

The straight or branched $C_1$-$C_6$ fluoroalkyl groups represented by $R^1$ include substituted forms of alkyl groups such as methyl, ethyl, n-propyl, isopropyl, n-butyl, sec-butyl, tert-butyl, tert-amyl, n-pentyl, and n-hexyl in which one or more hydrogen atoms are substituted by fluorine atoms. Specific examples include trifluoromethyl, 2,2,2-trifluoroethyl, 3,3,3-trifluoropropyl, 1,1,1,3,3,3-hexafluoroisopropyl, and 1,1,2,2,3,3,3-n-heptafluoropropyl.

Examples of the straight, branched or cyclic $C_1$-$C_6$ alkyl groups represented by $R^2$ include methyl, ethyl, n-propyl, isopropyl, n-butyl, sec-butyl, tert-butyl, tert-amyl, n-pentyl, n-hexyl, cyclopentyl, and cyclohexyl.

Examples of the straight, branched or cyclic $C_1$-$C_6$ alkylene groups represented by $R^3$ include the same alkyl groups as exemplified for $R^2$, with one hydrogen atom eliminated therefrom.

Examples of the straight, branched or cyclic $C_1$-$C_6$ alkyl groups represented by $R^4$ and $R^5$ include methyl, ethyl, n-propyl, isopropyl, n-butyl, sec-butyl, tert-butyl, tert-amyl, n-pentyl, n-hexyl, n-heptyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, cyclohexylbutyl, and adamantyl. Suitable fluoroalkyl groups include substituted forms of the foregoing alkyl groups in which one or more hydrogen atoms are substituted by fluorine atoms.

$R^6$ is an acid labile group which is selected from a variety of such groups. Examples of the acid labile group include groups of the following general formulae (AL-1) to (AL-3), trialkylsilyl groups in which each alkyl moiety has 1 to 6 carbon atoms, and oxoalkyl groups of 4 to 20 carbon atoms.

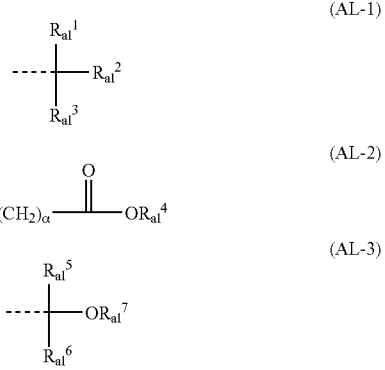

In these formulae and throughout the specification, a broken line denotes a valence bond.

$R_{a1}^1$, $R_{a1}^2$ and $R_{a1}^3$ may be the same or different and stand for straight, branched or cyclic $C_1$-$C_{20}$ hydrocarbon groups, typically alkyl groups, which may contain one or more heteroatom such as oxygen, sulfur or nitrogen, or bridged cyclic hydrocarbon groups. Alternatively, a pair of $R_{a1}^1$ and $R_{a1}^2$, $R_{a1}^1$ and $R_{a1}^3$, and $R_{a1}^2$ and $R_{a1}^3$, taken together, may form a ring. Each of $R_{a1}^1$, $R_{a1}^2$ and $R_{a1}^3$ is a straight or branched $C_1$-$C_{20}$ alkylene group when they form a ring. $R_{a1}^4$ and $R_{a1}^7$ stand for straight, branched or cyclic $C_1$-$C_{20}$ alkyl groups, which may contain one or more heteroatom such as oxygen, sulfur, nitrogen or fluorine. $R_{a1}^5$ and $R_{a1}^6$ stand for hydrogen or straight, branched or cyclic $C_1$-$C_{20}$ alkyl groups, which may contain one or more heteroatom such as oxygen, sulfur, nitrogen or fluorine. Alternatively, a pair of $R_{a1}^5$ and $R_{a1}^6$, $R_{a1}^5$ and $R_{a1}^7$, and $R_{a1}^6$ and $R_{a1}^7$, taken together, may form a ring. Each of $R_{a1}^5$, $R_{a1}^6$ and $R_{a1}^7$ is a straight or branched $C_1$-$C_{20}$ alkylene group when they form a ring. The subscript α is an integer of 0 to 6.

In formula (AL-1), illustrative examples of $R_{a1}^1$, $R_{a1}^2$ and $R_{a1}^3$ include methyl, ethyl, n-propyl, isopropyl, tert-butyl, cyclohexyl, cyclopentyl, norbornyl, adamantyl, and menthyl. The acid labile groups of formula (AL-1) are exemplified by the substituent groups shown below.

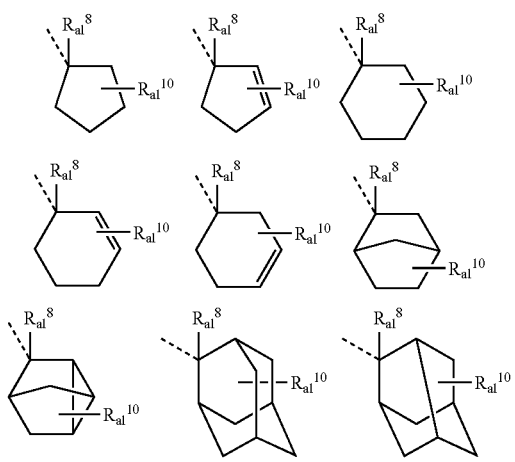

-continued

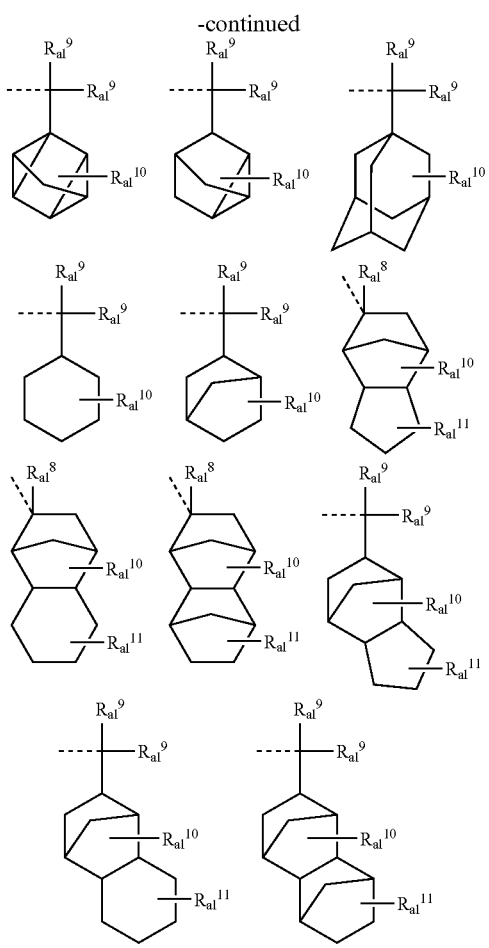

Herein, $R_{a1}^8$ and $R_{a1}^9$ stand for straight, branched or cyclic alkyl groups. $R_{a1}^{10}$ and $R_{a1}^{11}$ stand for hydrogen or monovalent hydrocarbon groups of 1 to 6 carbon atoms which may contain a heteroatom or be separated by a heteroatom and which may be straight, branched or cyclic.

Illustrative examples of $R_{a1}^8$ and $R_{a1}^9$ include methyl, ethyl, propyl, isopropyl, n-butyl, sec-butyl, n-pentyl, n-hexyl, cyclopropyl, cyclopropylmethyl, cyclobutyl, cyclopentyl, and cyclohexyl. Illustrative examples of $R_{a1}^{10}$ and $R_{a1}^{11}$ include methyl, ethyl, n-propyl, isopropyl, n-butyl, sec-butyl, n-pentyl, n-hexyl, hydroxymethyl, hydroxyethyl, methoxy, methoxymethoxy, ethoxy, and tert-butoxy. When $R_{a1}^{10}$ and $R_{a1}^{11}$ contain heteroatoms such as oxygen, sulfur or nitrogen, they may be contained, for example, in the form of —OH, —OR$_{a1}^{12}$, —O—, —S—, —S(=O)—, —NH$_2$, —NHR$_{a1}^{12}$, —N(R$_{a1}^{12}$)$_2$, —NH— or —NR$_{a1}^{12}$— wherein $R_{a1}^{12}$ is a $C_1$-$C_5$ alkyl group.

Illustrative examples of the acid labile groups of formula (AL-2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

In formula (AL-3), examples of the straight, branched or cyclic $C_1$-$C_{20}$ alkyl groups represented by $R_{a1}^5$ and $R_{a1}^6$ include methyl, ethyl, propyl, isopropyl, n-butyl, sec-butyl, tert-butyl, cyclopentyl, cyclohexyl, 2-ethylhexyl, and n-octyl. Examples of suitable hydrocarbon groups represented by $R_{a1}^7$ include substituted alkyl groups as shown below.

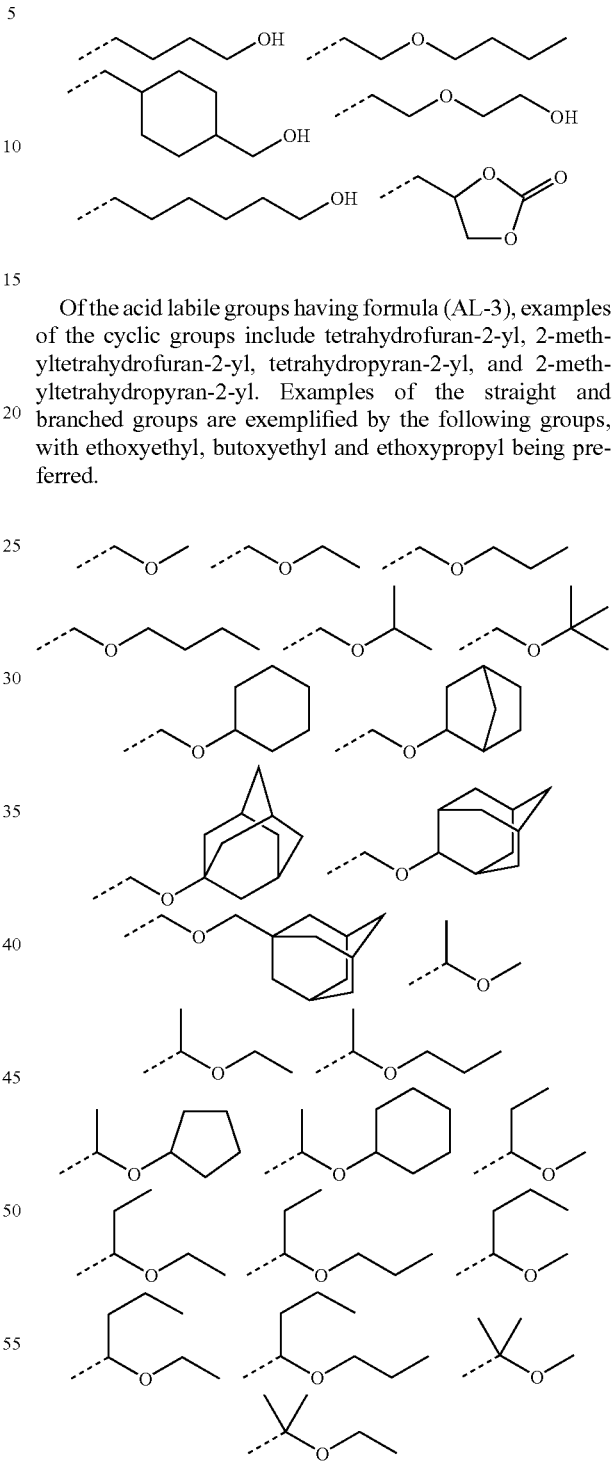

Of the acid labile groups having formula (AL-3), examples of the cyclic groups include tetrahydrofuran-2-yl, 2-methyltetrahydrofuran-2-yl, tetrahydropyran-2-yl, and 2-methyltetrahydropyran-2-yl. Examples of the straight and branched groups are exemplified by the following groups, with ethoxyethyl, butoxyethyl and ethoxypropyl being preferred.

The polymerizable ester compound of the invention can be prepared by acylating the hydroxyl group of an alcohol reactant as shown below. For the acylating reaction, any well-known ester preparing methods are applicable, for example, reaction with acylating agents, reaction with carboxylic acids, and transesterification reaction.

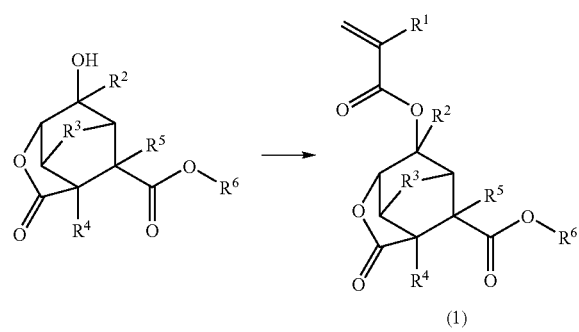

Herein $R^1$ is a fluorine atom or a straight or branched fluorinated alkyl group of 1 to 6 carbon atoms, $R^2$ is a hydrogen atom or a straight, branched or cyclic alkyl group of 1 to 8 carbon atoms, $R^3$ is an oxygen atom or a straight, branched or cyclic alkylene group of 1 to 6 carbon atoms, $R^4$ and $R^5$ each are a hydrogen atom or a straight, branched or cyclic alkyl or fluorinated alkyl group of 1 to 10 carbon atoms, and $R^6$ is a hydrogen atom or an acid labile group.

In the acylating reaction using acylating agents, the alcohol reactant is mixed with an organic solvent, and an acylating agent and a base are sequentially or simultaneously fed thereto whereupon reaction takes place. Examples of the acylating agent include acid halides such as acrylic chloride, methacrylic chloride, acrylic bromide, methacrylic bromide, α-fluoroacrylic chloride, and α-trifluoromethylacrylic chloride, and acid anhydrides such as acrylic anhydride, methacrylic anhydride, α-fluoroacrylic anhydride, α-trifluoromethylacrylic anhydride, acrylic acid/trifluoroacetic acid mixed acid anhydride, methacrylic acid/trifluoroacetic acid mixed acid anhydride, α-trifluoromethylacrylic acid/trifluoroacetic acid mixed acid anhydride, acrylic acid/p-nitrobenzoic acid mixed acid anhydride, methacrylic acid/p-nitrobenzoic acid mixed acid anhydride, ethyl acrylate/carbonic acid mixed acid anhydride, and ethyl methacrylate/carbonic acid mixed acid anhydride. Examples of the organic solvent used herein include chlorinated solvents such as methylene chloride, chloroform and trichloroethylene, hydrocarbons such as hexane, heptane, benzene, toluene, xylene and cumene, ethers such as dibutyl ether, diethylene glycol diethyl ether, diethylene glycol dimethyl ether, tetrahydrofuran, and 1,4-dioxane, nitriles such as acetonitrile, ketones such as acetone and 2-butanone, esters such as ethyl acetate and n-butyl acetate, and aprotic polar solvents such as N,N-dimethylformamide, dimethyl sulfoxide, and hexamethylphosphoric triamide, alone or in admixture of any. Examples of the base include triethylamine, diisopropylethylamine, N,N-dimethylaniline, pyridine, and 4-dimethylaminopyridine. An appropriate reaction temperature may be selected depending on the type of acylating agent used and other reaction conditions. The reaction temperature is preferably from −50° C. to approximately the boiling point of the solvent, more preferably from −20° C. to room temperature. An appropriate amount of the acylating agent used is from 1 to 40 moles, more preferably 1 to 5 moles per mole of the alcohol reactant, though it depends on the structure of the agent.

The acylating reaction with carboxylic acids is a dehydrating reaction from a corresponding carboxylic acid, i.e., any of acrylic acid, methacrylic acid and α-trifluoromethylacrylic acid and the alcohol reactant, which is generally performed in the presence of an acid catalyst. An appropriate amount of carboxylic acid used is 1 to 40 moles, more preferably 1 to 5 moles per mole of the alcohol reactant, though it depends on the structure of acid. Examples of the acid catalyst include inorganic acids such as hydrochloric acid, hydrobromic acid, sulfuric acid, and nitric acid, and organic acids such as oxalic acid, trifluoroacetic acid, methanesulfonic acid, benzenesulfonic acid, and p-toluenesulfonic acid, alone or in admixture of any. An appropriate amount of the acid catalyst used is 0.001 to 1 mole, more preferably 0.01 to 0.05 mole per mole of the alcohol reactant. Examples of the solvent used are as exemplified above for the reaction with the acylating agent. The reaction temperature is preferably from −50° C. to approximately the boiling point of the solvent although it depends on the type of carboxylic acid used and other reaction conditions. The reaction may also be performed in a solvent comprising a hydrocarbon such as hexane, heptane, benzene, toluene, xylene or cumene, by heating the system around the boiling point of the solvent, while azeotroping the formed water out of the system. In this embodiment, the water may be distilled off by reflux heating under atmospheric pressure, or the water be distilled off at a lower temperature than the boiling point and reduced pressure.

The transesterification is implemented by reacting the alcohol reactant with a corresponding carboxylic acid ester, i.e., any of acrylate, methacrylate and α-trifluoromethylacrylate in the presence of a catalyst and removing the alcohol formed. The carboxylic acid esters used are preferably primary alkyl esters. Inter alia, methyl, ethyl and n-propyl esters are preferred because of low cost and smooth progress of reaction. An appropriate amount of carboxylic acid ester used is 1 to 40 moles, more preferably 1 to 5 moles per mole of the alcohol reactant, though it depends on the structure of ester. Examples of the catalyst include inorganic acids such as hydrochloric acid, hydrobromic acid, sulfuric acid, and nitric acid, organic acids such as oxalic acid, trifluoroacetic acid, methanesulfonic acid, benzenesulfonic acid, and p-toluenesulfonic acid, bases such as sodium methoxide, sodium ethoxide, potassium t-butoxide, and 4-dimethylaminopyridine, salts such as sodium cyanide, potassium cyanide, sodium acetate, potassium acetate, calcium acetate, tin acetate, aluminum acetate, aluminum acetoacetate, alumina, and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide, alone or in admixture of any. An appropriate amount of the catalyst used is 0.001 to 20 moles, more preferably 0.01 to 0.05 mole per mole of the alcohol reactant. The reaction may be performed in a solventless system (the reagent, carboxylic acid ester itself may serve as a solvent), which is preferred in that extra operations such as concentration and solvent recovery are eliminated. A solvent may be used in a supplemental manner for the purpose of preventing polymerization of the target compound and reagent. Examples of the solvent, if used, include hydrocarbons such as hexane, heptane, benzene, toluene, xylene and cumene, and ethers such as dibutyl ether, diethylene glycol diethyl ether, diethylene glycol dimethyl ether, tetrahydrofuran, and 1,4-dioxane, alone or in admixture. An appropriate reaction temperature may be selected depending on the type of carboxylic acid ester used and other reaction conditions. Usually, the reaction is performed at elevated temperature. Better results are obtained when the reaction is performed at a temperature approximate to the boiling point of a low boiling point alcohol formed by transesterification reaction such as methanol, ethanol or 1-propanol, whereby the alcohol formed is distilled off during the reaction. The alcohol may be distilled off at a lower temperature than the boiling point and reduced pressure.

It is desired for higher yields that the time of acylating reaction is determined by monitoring the progress of reaction by thin-layer chromatography (TLC) or gas chromatography (GC). The reaction time is usually about 0.1 hour to about 240 hours. After the completion of reaction, the target polymerizable ester compound (1) is recovered from the reaction mixture by a conventional post-treatment such as aqueous work-up or concentration. If necessary, the ester compound (1) can be purified by any conventional technique such as recrystallization, chromatography or distillation.

Illustrative, non-limiting examples of the polymerizable ester compound (1) are given below.

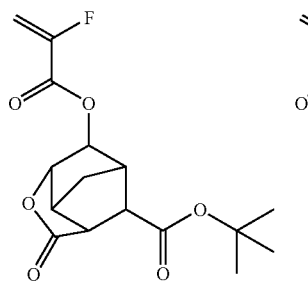

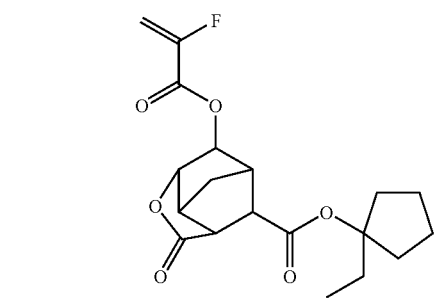

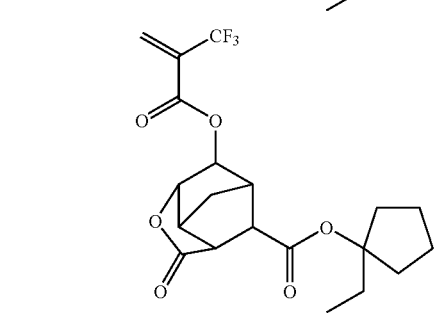

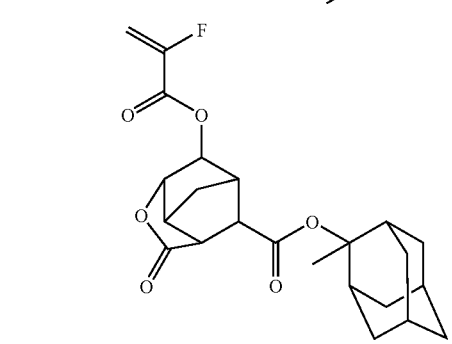

-continued

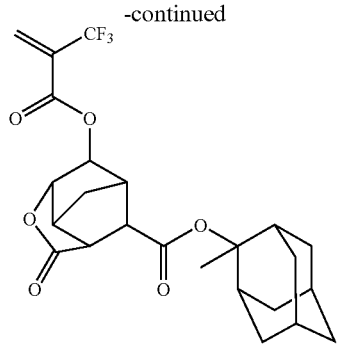

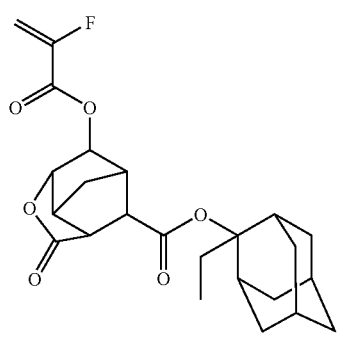

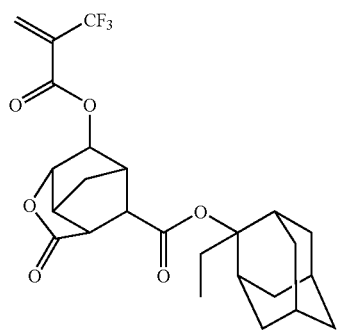

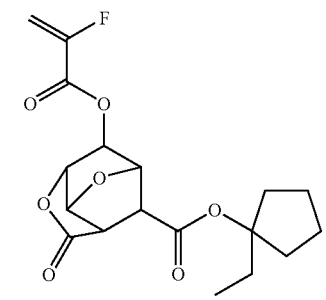

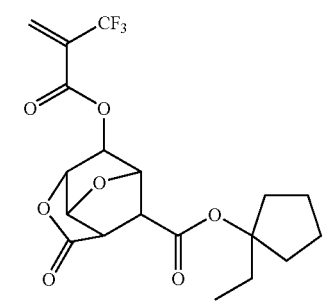

-continued

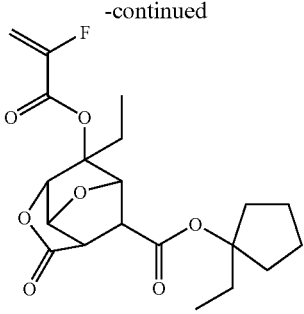

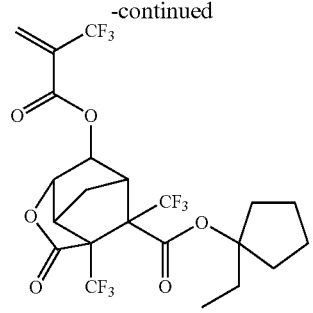

Polymer

The polymer of the invention is characterized by comprising recurring units having the general formula (2).

(2)

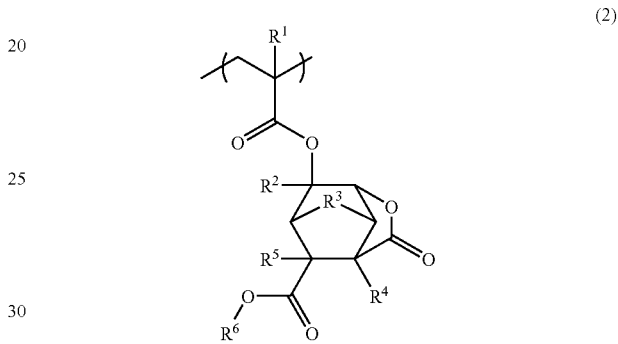

Herein $R^1$ is a fluorine atom or a straight or branched fluorinated alkyl group of 1 to 6 carbon atoms, $R^2$ is a hydrogen atom or a straight, branched or cyclic alkyl group of 1 to 8 carbon atoms, $R^3$ is an oxygen atom or a straight, branched or cyclic alkylene group of 1 to 6 carbon atoms, $R^4$ and $R^5$ each are a hydrogen atom or a straight, branched or cyclic alkyl or fluorinated alkyl group of 1 to 10 carbon atoms, and $R^6$ is a hydrogen atom or an acid labile group.

The straight or branched $C_1$-$C_6$ fluoroalkyl groups represented by $R^1$, the straight, branched or cyclic $C_1$-$C_6$ alkyl groups represented by $R^2$, the straight, branched or cyclic $C_1$-$C_6$ alkylene groups represented by $R^3$, the straight, branched or cyclic $C_1$-$C_{10}$ alkyl or fluoroalkyl groups represented by $R^4$ and $R^5$, and the acid labile group represented by $R^6$ are the same as previously described for the polymerizable ester compounds.

The preferred polymer of the invention comprises recurring units having the general formula (2) and recurring units having the general formula (3).

(2)

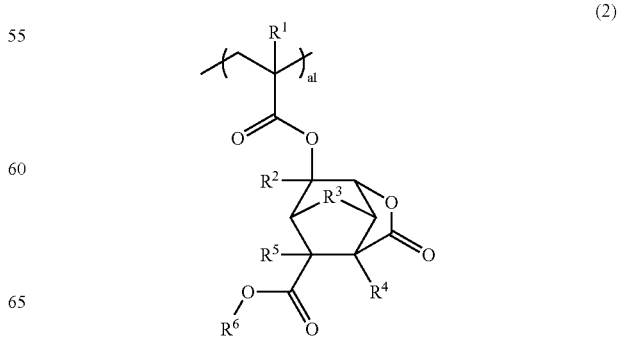

-continued (3)

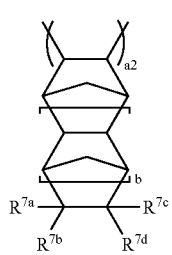

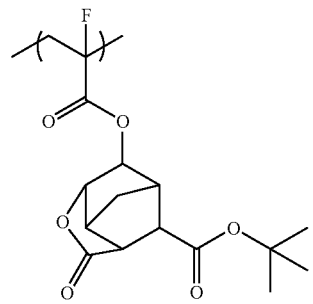

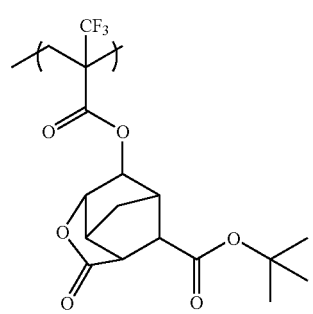

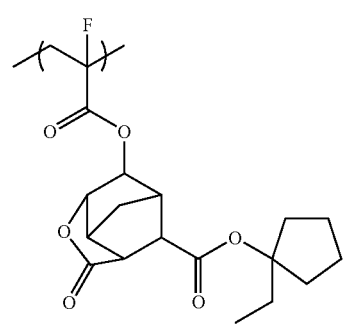

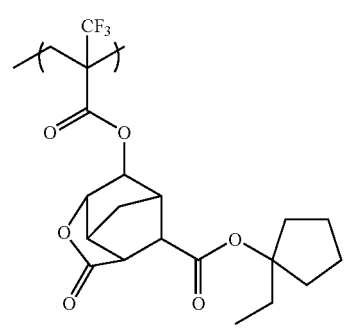

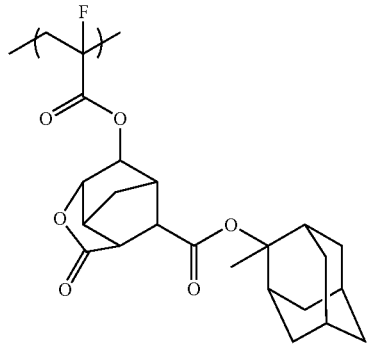

Herein $R^1$ is a fluorine atom or a straight or branched fluorinated alkyl group of 1 to 6 carbon atoms, $R^2$ is a hydrogen atom or a straight, branched or cyclic alkyl group of 1 to 8 carbon atoms, $R^3$ is an oxygen atom or a straight, branched or cyclic alkylene group of 1 to 6 carbon atoms, $R^4$ and $R^5$ each are a hydrogen atom or a straight, branched or cyclic alkyl or fluorinated alkyl group of 1 to 10 carbon atoms, $R^6$ is a hydrogen atom or an acid labile group, $R^{7a}$, $R^{7b}$, $R^{7c}$, and $R^{7d}$ each are a hydrogen atom, fluorine atom, straight, branched or cyclic alkyl or fluorinated alkyl group of 1 to 10 carbon atoms, —$R^8$—C(=O)—OR$^9$, or —$R^8$—OR$^9$, $R^8$ is a single bond or a straight, branched or cyclic alkylene or fluorinated alkylene group of 1 to 10 carbon atoms, $R^9$ is a hydrogen atom or an acid labile group, the subscripts a1 and a2 are 0<a1<1, 0<a2<1, and 0<a1+a2≦1.

The straight or branched $C_1$-$C_6$ fluoroalkyl groups represented by $R^1$, the straight, branched or cyclic $C_1$-$C_6$ alkyl groups represented by $R^2$, the straight, branched or cyclic $C_1$-$C_6$ alkylene groups represented by $R^3$, the straight, branched or cyclic $C_1$-$C_{10}$ alkyl or fluoroalkyl groups represented by $R^4$ and $R^5$, and the acid labile group represented by $R^6$ are the same as previously described for the polymerizable ester compounds. Examples of the straight, branched or cyclic $C_1$-$C_{10}$ alkyl group represented by $R^{7a}$, $R^{7b}$, $R^{7c}$, and $R^{7d}$ include methyl, ethyl, n-propyl, isopropyl, n-butyl, sec-butyl, tert-butyl, tert-amyl, n-pentyl, n-hexyl, n-heptyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, cyclohexylbutyl, and adamantyl; and examples of the fluoroalkyl group include substituted forms of the foregoing alkyl groups in which one or more hydrogen atoms are substituted by fluorine atoms. Examples of the straight, branched or cyclic $C_1$-$C_{10}$ alkylene or fluoroalkylene groups represented by $R^8$ correspond to the foregoing alkyl or fluoroalkyl groups with one hydrogen atom eliminated. The acid labile group represented by $R^9$ are the same as $R^6$ in the polymerizable ester compounds of formula (1).

It is understood that although the recurring units of formula (2) include a multiplicity of variations depending on combinations of $R^1$ through $R^6$, formula (2) collectively represents all such recurring units. Although the recurring units of formula (3) include a multiplicity of variations depending on combinations of $R^{7a}$ through $R^9$, formula (3) collectively represents all such recurring units. The polymer of the invention may contain recurring units of only one type or recurring units of more than one type for each formula.

Illustrative, non-limiting examples of the recurring units of formula (2) are given below.

-continued
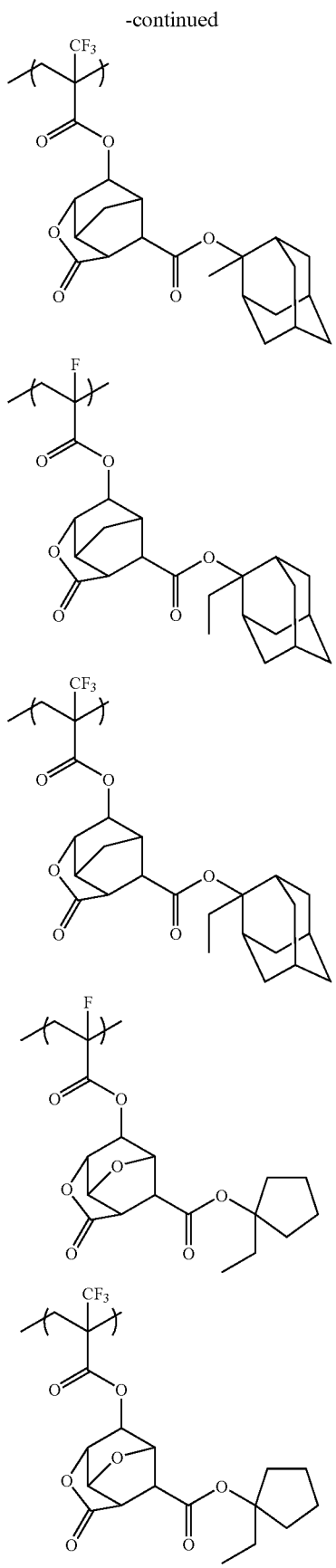
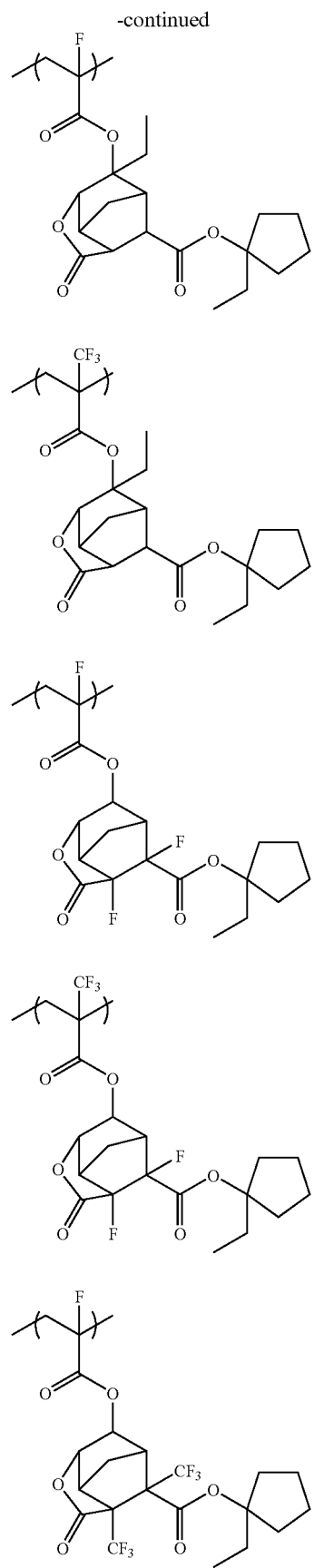

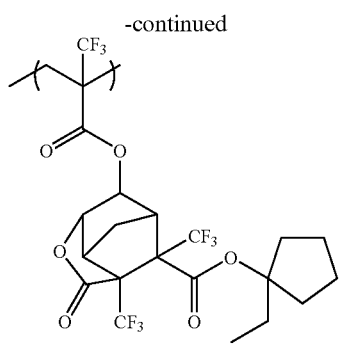
Illustrative, non-limiting examples of the recurring units of formula (3) are given below.
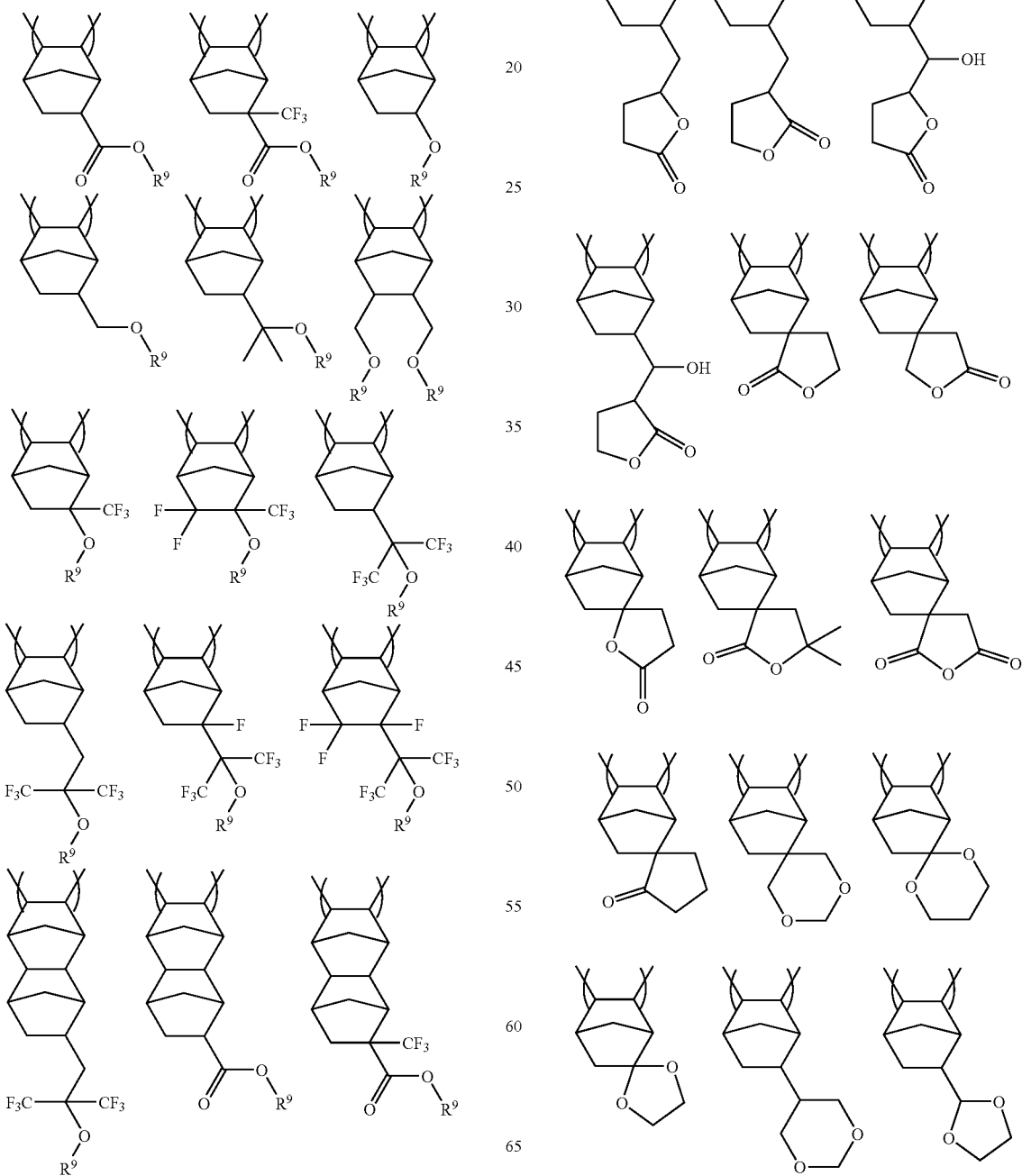

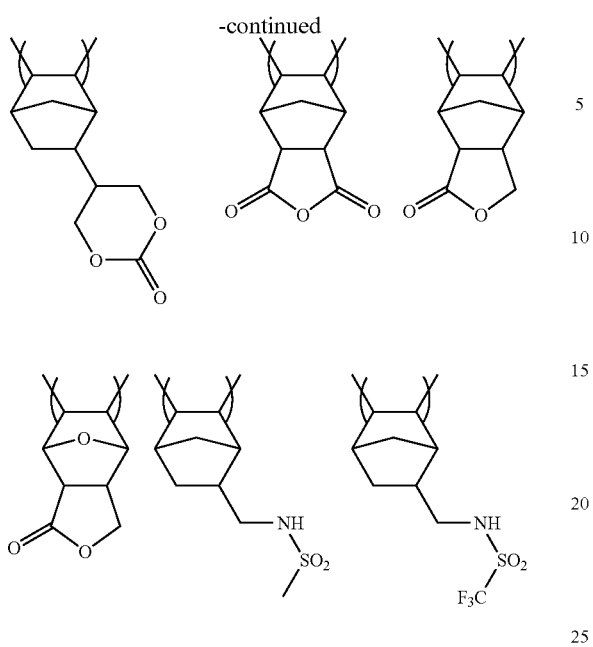

In the above formulae, $R^9$ is hydrogen or an acid labile group.

In the polymer of the invention comprising the recurring units of formulae (2) and (3), recurring units of the general formula (4) may be incorporated for the purpose of improving the resolution characteristics of a resist film and the transparency, etching resistance, adhesion and water repellency of a resin.

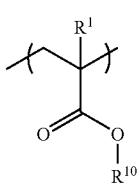
(4)

Herein $R^1$ is a fluorine atom or a straight or branched fluorinated alkyl group of 1 to 6 carbon atoms, and $R^{10}$ is a hydrogen atom, a straight, branched or cyclic fluorinated alkyl group of 1 to 10 carbon atoms, an acid labile group, or an adhesive group.

Examples of the straight, branched or cyclic $C_1$-$C_{10}$ fluoroalkyl group represented by $R^{10}$ include substituted forms of methyl, ethyl, n-propyl, isopropyl, n-butyl, sec-butyl, tert-butyl, tert-amyl, n-pentyl, n-hexyl, n-heptyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, cyclohexylbutyl, and adamantyl groups in which one or more hydrogen atoms are substituted by fluorine atoms. The acid labile group represented by $R^{10}$ are the same as $R^6$ in the polymerizable ester compounds of formula (1).

The adhesive group represented by $R^{10}$ is selected from a variety of such groups, preferably from the groups shown below.

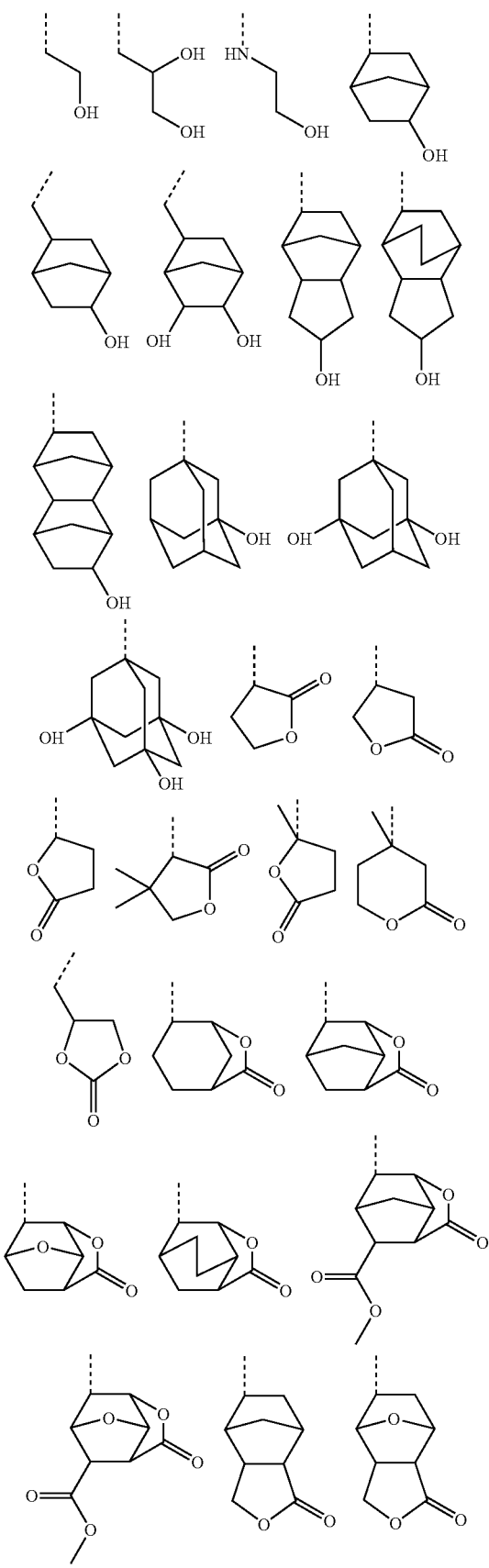

-continued

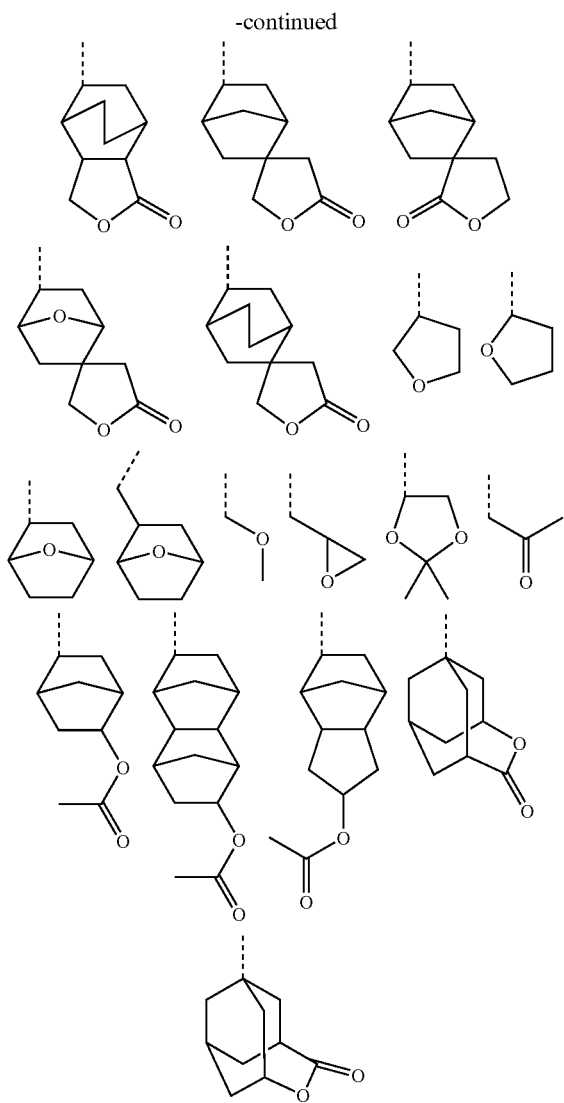

It is understood that although the recurring units of formula (4) include a multiplicity of variations depending on combinations of $R^1$ and $R^{10}$, formula (4) collectively represents all such recurring units. The polymer of the invention may contain recurring units of only one type or recurring units of more than one type of that formula.

In the polymer of the invention comprising the recurring units of formulae (2) and (3) and/or (4), recurring units of one or more types as shown below may further be incorporated for the purpose of improving the resolution characteristics of a resist film and the transparency, etching resistance, adhesion and water repellency of a resin.

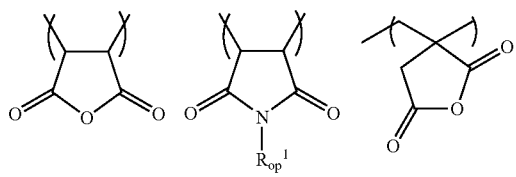

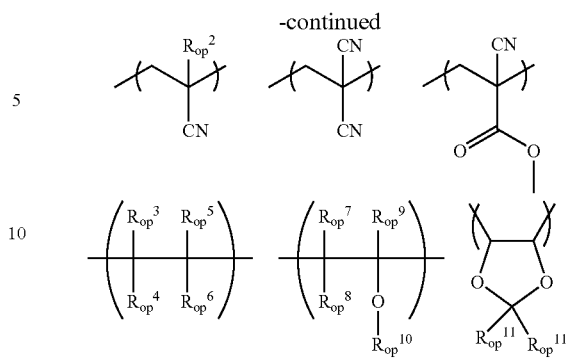

Herein, $R_{op}^1$ and $R_{op}^2$ each are a hydrogen atom or a straight, branched or cyclic $C_1$-$C_{10}$ alkyl or fluoroalkyl group. $R_{op}^3$ to $R_{op}^6$ each are a hydrogen atom, fluorine atom or a $C_1$-$C_4$ fluoroalkyl group, and at least one of $R_{op}^3$ to $R_{op}^6$ contains a fluorine atom(s). $R_{op}^7$, $R_{op}^8$, and $R_{op}^9$ each are a hydrogen atom, fluorine atom or a straight, branched or cyclic $C_1$-$C_{10}$ alkyl or fluoroalkyl group. $R_{op}^{10}$ is a hydrogen atom, or a straight, branched or cyclic $C_1$-$C_{10}$ alkyl or fluoroalkyl group which may contain a heteroatom. Two or more of $R_{op}^7$, $R_{op}^8$, $R_{op}^9$ and $R_{op}^{10}$ may bond together to form a ring with the carbon and oxygen atoms to which they are attached. $R_{op}^{11}$ and $R_{op}^{12}$ each are a hydrogen atom, methyl or trifluoromethyl group.

Examples of the straight, branched or cyclic $C_1$-$C_{10}$ alkyl group represented by $R_{op}^1$, $R_{op}^2$, $R_{op}^7$ to $R_{op}^{10}$ include methyl, ethyl, n-propyl, isopropyl, n-butyl, sec-butyl, tert-butyl, tert-amyl, n-pentyl, n-hexyl, n-heptyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, cyclohexylbutyl, and adamantyl; and examples of the fluoroalkyl group include substituted forms of the foregoing alkyl groups in which one or more hydrogen atoms are substituted by fluorine atoms. Examples of the $C_1$-$C_4$ fluoroalkyl group represented by $R_{op}^3$ to $R_{op}^6$ include substituted forms of methyl, ethyl, n-propyl, isopropyl, n-butyl, sec-butyl, and tert-butyl groups in which one or more hydrogen atoms are substituted by fluorine atoms.

The polymer of the invention is generally synthesized by dissolving monomers corresponding to the recurring units having formulae (2), (3) and (4) and monomers corresponding to the adhesion or transparency-improving units in a solvent, adding a catalyst thereto, and effecting polymerization reaction while heating or cooling the system if necessary. The polymerization reaction also depends on the type of initiator or catalyst, trigger means (including light, heat, radiation and plasma), and polymerization conditions (including temperature, pressure, concentration, solvent, and additives). Commonly used for preparation of the polymers of the invention are radical copolymerization of triggering polymerization with radicals of 2,2'-azobisisobutyronitrile (AIBN) or the like and ionic polymerization (anionic polymerization) in the presence of alkyllithium and similar catalysts. These polymerization reactions may be carried out in a conventional manner.

The initiator used for radical polymerization is not critical. Exemplary initiators include azo compounds such as AIBN, 2,2'-azobis(4-methoxy-2,4-dimethylvaleronitrile), 2,2'-azobis(2,4-dimethylvaleronitrile), and 2,2'-azobis(2,4,4-trimethylpentane); and peroxide compounds such as tert-butyl peroxypivalate, lauroyl peroxide, benzoyl peroxide and tert-butyl peroxylaurate. Water-soluble initiators include persulfate salts such as potassium persulfate, and redox combinations of potassium persulfate or peroxides such as hydrogen peroxide with reducing agents such as sodium sulfite. The amount of the polymerization initiator used is determined as appropriate in accordance with such factors as the identity of initiator and polymerization conditions, although the amount is often in the range of about 0.001 to 10 mol %, especially about 0.01 to 5 mol % based on the total moles of monomers to be polymerized.

Any of well-known molecular weight modifiers such as dodecylmercaptan and 2-mercaptoethanol may be used in the polymerization system, preferably in an amount of 0.01 to 10 mol %.

For the polymerization reaction, a solvent may be used. The polymerization solvent used herein is preferably one which does not interfere with the polymerization reaction. Typical solvents include ester solvents such as ethyl acetate, n-butyl acetate and γ-butyrolactone, ketone solvents such as acetone, methyl ethyl ketone and methyl isobutyl ketone, aliphatic or aromatic hydrocarbon solvents such as toluene, xylene and cyclohexane, alcohol solvents such as isopropyl alcohol and ethylene glycol monomethyl ether, and ether solvents such as diethyl ether, dioxane, and tetrahydrofuran (THF). These solvents may be used alone or in admixture of two or more. The amount of polymerization solvent used may be altered depending on the desired degree of polymerization (or molecular weight), the amount of initiator added, polymerization temperature and other conditions. Most often, the solvent is added in such amounts as to give a concentration of 0.1 to 95% by weight, especially 5 to 90% by weight of the monomers to be polymerized.

The temperature of polymerization reaction varies in accordance with the identity of polymerization initiator and the boiling point of the solvent although it is often preferably in the range of about 20 to 200° C., and especially about 50 to 140° C. Any desired reactor or vessel may be used for the polymerization reaction.

From the solution or dispersion of the polymer thus obtained, the organic solvent or water serving as the reaction medium is removed by any of well-known techniques. Suitable techniques include, for example, re-precipitation followed by filtration, and heat distillation under vacuum.

Desirably the polymer has a weight average molecular weight (Mw) of about 1,000 to about 500,000, and especially about 2,000 to about 30,000, as determined by gel permeation chromatography-(GPC) using polystyrene standards.

In the polymers of the invention wherein U1 stands for a monomer corresponding to units of formula (2), U2 stands for a monomer corresponding to units of formula (3), U3 stands for a monomer corresponding to units of formula (4), and U4 stands for a monomer corresponding to adhesion and transparency-improving units, a molar proportion of U1 through U4, with the proviso that U1+U2+U3+U4=U, is preferably determined so as to meet:

$0<U1/U\leq1$, more preferably $0.2<U1/U\leq0.8$, $0\leq U2/U\leq0.6$, more preferably $0.2\leq U2/U\leq0.5$, $0\leq U3/U\leq0.5$, more preferably $0.1\leq U3/U\leq0.4$, and $0\leq U4/U\leq0.3$, more preferably $0\leq U4/U\leq0.1$.

The polymer of the invention can be used as a base resin in resist compositions, typically chemically amplified resist compositions, and more typically chemically amplified positive working resist compositions and as a base resin for resist protective film. It is understood that the polymer of the invention may be admixed with another polymer for the purpose of altering the dynamic properties, thermal properties, alkali solubility and other physical properties of polymer film. The type of the other polymer which can be admixed is not critical. Any of polymers known to be useful in resist use may be admixed in any desired proportion.

Resist Composition

As long as the polymer of the invention is used as a base resin, the resist composition of the invention may be prepared using well-known components. In a preferred embodiment, the chemically amplified positive resist composition comprises (A) the above-defined polymer as a base resin, (B) an organic solvent, and (C) a photoacid generator. In the resist composition, there may be further formulated (D) a basic compound and/or (E) a dissolution inhibitor.

Component (B)

The organic solvent used as component (B) in the invention may be any organic solvent in which the base resin (inventive polymer), photoacid generator, and other components are soluble. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, propylene glycol monoethyl ether, propylene glycol dimethyl ether, ethylene glycol monomethyl ether, ethylene glycol monoethyl ether, and diethylene glycol dimethyl ether; and esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate.

These solvents may be used alone or in combinations of two or more thereof. Of the above organic solvents, preferred are diethylene glycol dimethyl ether and 1-ethoxy-2-propanol, in which the photoacid generator is most soluble, and propylene glycol monomethyl ether acetate (PGMEA) which is safe, and mixtures thereof.

The solvent is preferably used in an amount of about 300 to 10,000 parts by weight, more preferably about 500 to 5,000 parts by weight per 100 parts by weight of the base resin.

Component (C)

The photoacid generators used herein include (i) onium salts of the formula (P1a-1), (P1a-2) or (P1b), (ii) diazomethane derivatives of the formula (P2), (iii) glyoxime derivatives of the formula (P3), (iv) bissulfone derivatives of the formula (P4), (v) sulfonic acid esters of N-hydroxyimide compounds of the formula (P5), (vi) β-ketosulfonic acid derivatives, (vii) disulfone derivatives, (viii) nitrobenzylsulfonate derivatives, and (ix) sulfonate derivatives.

These acid generators are described in detail.

(i) Onium Salts of Formula (P1a-1), (P1a-2) or (P1b):

(P1a-1)

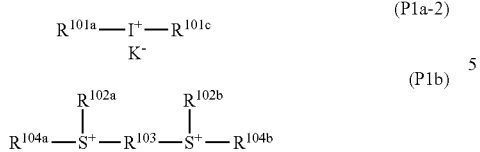

$$R^{101a}-I^+-R^{101c} \quad (P1a-2)$$
$$K^-$$

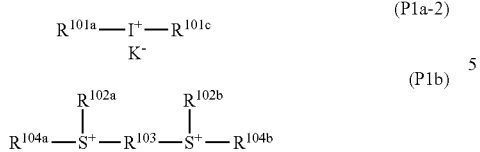

(P1b)

Herein, $R^{101a}$, $R^{101b}$, and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$ taken together, may form a ring. $R^{101b}$ and $R^{101c}$ are alkylene groups of 1 to 6 carbon atoms when they form a ring. $R^{102a}$ and $R^{102b}$ independently represent straight, branched or cyclic alkyl groups of 1 to 8 carbon atoms. $R^{103}$ represents a straight, branched or cyclic alkylene group of 1 to 10 carbon atoms. $R^{104a}$ and $R^{104b}$ independently represent 2-oxoalkyl groups of 3 to 7 carbon atoms. $K^-$ is a non-nucleophilic counter ion.

$R^{101a}$, $R^{101b}$, and $R^{101c}$ may be the same or different and are illustrated below. Exemplary alkyl-groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl.

Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

(ii) Diazomethane Derivatives of Formula (P2)

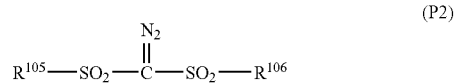

(P2)

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime Derivatives of Formula (P3)

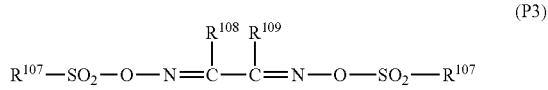

(P3)

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone Derivatives of Formula (P4)

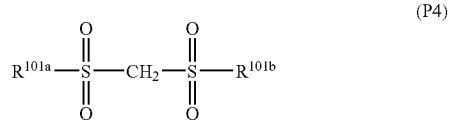

(P4)

Herein, $R^{101a}$ and $R^{101b}$ are independently straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Examples of $R^{101a}$ and $R^{101b}$ are as described above for the onium salts (i).

(v) Sulfonic Acid Esters of N-Hydroxyimide Compounds of Formula (P5)

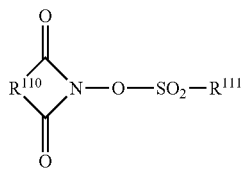

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$, is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), heteroaromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, ethylene, trimethylene, tetramethylene, phenylethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; the alkoxy groups of 1 to 4 carbon atoms include methoxy, ethoxy, propoxy, isopropoxy, n-butoxy, isobutoxy, and tert-butoxy; the phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl; the hetero-aromatic groups of 3 to 5 carbon atoms include pyridyl and furyl.

Illustrative examples of the acid generators (i) to (ix) include:
onium salts such as
diphenyliodonium trifluoromethanesulfonate,
(p-tert-butoxyphenyl)phenyliodonium trifluoromethanesulfonate,
diphenyliodonium p-toluenesulfonate,
(p-tert-butoxyphenyl)phenyliodonium p-toluenesulfonate,
triphenylsulfonium trifluoromethanesulfonate,
(p-tert-butoxyphenyl)diphenylsulfonium trifluoromethanesulfonate,
bis(p-tert-butoxyphenyl)phenylsulfonium trifluoromethanesulfonate,
tris(p-tert-butoxyphenyl)sulfonium trifluoromethanesulfonate,
triphenylsulfonium p-toluenesulfonate,
(p-tert-butoxyphenyl)diphenylsulfonium p-toluenesulfonate,
bis(p-tert-butoxyphenyl)phenylsulfonium p-toluenesulfonate,
tris(p-tert-butoxyphenyl)sulfonium p-toluenesulfonate,
triphenylsulfonium nonafluorobutanesulfonate,
triphenylsulfonium butanesulfonate,
trimethylsulfonium trifluoromethanesulfonate,
trimethylsulfonium p-toluenesulfonate,
cyclohexylmethyl(2-oxocyclohexyl)sulfonium trifluoromethane-sulfonate,
cyclohexylmethyl(2-oxocyclohexyl)sulfonium p-toluenesulfonate,
dimethylphenylsulfonium trifluoromethanesulfonate,
dimethylphenylsulfonium p-toluenesulfonate,
dicyclohexylphenylsulfonium trifluoromethanesulfonate,
dicyclohexylphenylsulfonium p-toluenesulfonate,
trinaphthylsulfonium trifluoromethanesulfonate,
cyclohexylmethyl(2-oxocyclohexyl)sulfonium trifluoromethane-sulfonate,
(2-norbornyl)methyl(2-oxocyclohexyl)sulfonium trifluoromethanesulfonate,
ethylenebis[methyl(2-oxocyclopentyl)sulfonium trifluoromethanesulfonate], and
1,2'-naphthylcarbonylmethyltetrahydrothiophenium triflate;
diazomethane derivatives such as
bis(benzenesulfonyl)diazomethane,
bis(p-toluenesulfonyl)diazomethane,
bis(xylenesulfonyl)diazomethane,
bis(cyclohexylsulfonyl)diazomethane,
bis(cyclopentylsulfonyl)diazomethane,
bis(n-butylsulfonyl)diazomethane,
bis(isobutylsulfonyl)diazomethane,
bis(sec-butylsulfonyl)diazomethane,
bis(n-propylsulfonyl)diazomethane,
bis(isopropylsulfonyl)diazomethane,
bis(tert-butylsulfonyl)diazomethane,
bis(n-amylsulfonyl)diazomethane,
bis(isoamylsulfonyl)diazomethane,
bis(sec-amylsulfonyl)diazomethane,
bis(tert-amylsulfonyl)diazomethane,
1-cyclohexylsulfonyl-1-(tert-butylsulfonyl)diazomethane,
1-cyclohexylsulfonyl-1-(tert-amylsulfonyl)diazomethane, and
1-tert-amylsulfonyl-1-(tert-butylsulfonyl)diazomethane;
glyoxime derivatives such as
bis-O-(p-toluenesulfonyl)-α-dimethylglyoxime,
bis-O-(p-toluenesulfonyl)-α-diphenylglyoxime,
bis-O-(p-toluenesulfonyl)-α-dicyclohexylglyoxime,
bis-O-(p-toluenesulfonyl)-2,3-pentanedioneglyoxime,
bis-O-(p-toluenesulfonyl)-2-methyl-3,4-pentanedioneglyoxime,
bis-O-(n-butanesulfonyl)-α-dimethylglyoxime,
bis-O-(n-butanesulfonyl)-α-diphenylglyoxime,
bis-O-(n-butanesulfonyl)-α-dicyclohexylglyoxime,
bis-O-(n-butanesulfonyl)-2,3-pentanedioneglyoxime,
bis-O-(n-butanesulfonyl)-2-methyl-3,4-pentanedioneglyoxime,
bis-O-(methanesulfonyl)-α-dimethylglyoxime,
bis-O-(trifluoromethanesulfonyl)-α-dimethylglyoxime,
bis-O-(1,1,1-trifluoroethanesulfonyl)-α-dimethylglyoxime,
bis-O-(tert-butanesulfonyl)-α-dimethylglyoxime, bis-O-(perfluorooctanesulfonyl)-α-dimethylglyoxime,
bis-O-(cyclohexanesulfonyl)-α-dimethylglyoxime,
bis-O-(benzenesulfonyl)-α-dimethylglyoxime,
bis-O-(p-fluorobenzenesulfonyl)-α-dimethylglyoxime,
bis-O-(p-tert-butylbenzenesulfonyl)-α-dimethylglyoxime,
bis-O-(xylenesulfonyl)-α-dimethylglyoxime, and
bis-O-(camphorsulfonyl)-α-dimethylglyoxime;
  bissulfone derivatives such as
bisnaphthylsulfonylmethane, bistrifluoromethylsulfonylmethane,
bismethylsulfonylmethane, bisethylsulfonylmethane,
bispropylsulfonylmethane, bisisopropylsulfonylmethane,
bis-p-toluenesulfonylmethane, and bisbenzenesulfonylmethane;
  β-ketosulfonic acid derivatives such as
2-cyclohexylcarbonyl-2-(p-toluenesulfonyl)propane and
2-isopropylcarbonyl-2-(p-toluenesulfonyl)propane;
  disulfone derivatives such as diphenyl disulfone and dicyclohexyl disulfone;
  nitrobenzyl sulfonate derivatives such as
2,6-dinitrobenzyl p-toluenesulfonate and
2,4-dinitrobenzyl p-toluenesulfonate;
  sulfonic acid ester derivatives such as
1,2,3-tris(methanesulfonyloxy)benzene,
1,2,3-tris(trifluoromethanesulfonyloxy)benzene, and
1,2,3-tris(p-toluenesulfonyloxy)benzene; and
  sulfonic acid esters of N-hydroxyimides such as
N-hydroxysuccinimide methanesulfonate,
N-hydroxysuccinimide trifluoromethanesulfonate,
N-hydroxysuccinimide ethanesulfonate,
N-hydroxysuccinimide 1-propanesulfonate,
N-hydroxysuccinimide 2-propanesulfonate,
N-hydroxysuccinimide 1-pentanesulfonate,
N-hydroxysuccinimide 1-octanesulfonate,
N-hydroxysuccinimide p-toluenesulfonate,
N-hydroxysuccinimide p-methoxybenzenesulfonate,
N-hydroxysuccinimide 2-chloroethanesulfonate,
N-hydroxysuccinimide benzenesulfonate,
N-hydroxysuccinimide 2,4,6-trimethylbenzenesulfonate,
N-hydroxysuccinimide 1-naphthalenesulfonate,
N-hydroxysuccinimide 2-naphthalenesulfonate,
N-hydroxy-2-phenylsuccinimide methanesulfonate,
N-hydroxymaleimide methanesulfonate,
N-hydroxymaleimide ethanesulfonate,
N-hydroxy-2-phenylmaleimide methanesulfonate,
N-hydroxyglutarimide methanesulfonate,
N-hydroxyglutarimide benzenesulfonate,
N-hydroxyphthalimide methanesulfonate,
N-hydroxyphthalimide benzenesulfonate,
N-hydroxyphthalimide trifluoromethanesulfonate,
N-hydroxyphthalimide p-toluenesulfonate,
N-hydroxynaphthalimide methanesulfonate,
N-hydroxynaphthalimide benzenesulfonate,
N-hydroxy-5-norbornene-2,3-dicarboxyimide methanesulfonate,
N-hydroxy-5-norbornene-2,3-dicarboxyimide trifluoromethane-sulfonate, and
N-hydroxy-5-norbornene-2,3-dicarboxyimide p-toluenesulfonate.

Preferred among these acid generators are onium salts such as triphenylsulfonium trifluoromethanesulfonate, (p-tert-butoxyphenyl)diphenylsulfonium trifluoromethane-sulfonate, tris(p-tert-butoxyphenyl)sulfonium trifluoromethane-sulfonate,
triphenylsulfonium p-toluenesulfonate,
(p-tert-butoxyphenyl)diphenylsulfonium p-toluenesulfonate,
tris(p-tert-butoxyphenyl)sulfonium p-toluenesulfonate,
trinaphthylsulfonium trifluoromethanesulfonate,
cyclohexylmethyl(2-oxocyclohexyl)sulfonium trifluoromethane-sulfonate,
(2-norbornyl)methyl(2-oxocylohexyl)sulfonium trifluoromethanesulfonate, and
1,2'-naphthylcarbonylmethyltetrahydrothiophenium triflate;
  diazomethane derivatives such as
bis(benzenesulfonyl)diazomethane,
bis(p-toluenesulfonyl)diazomethane,
bis(cyclohexylsulfonyl)diazomethane,
bis(n-butylsulfonyl)diazomethane,
bis(isobutylsulfonyl)diazomethane,
bis(sec-butylsulfonyl)diazomethane,
bis(n-propylsulfonyl)diazomethane,
bis(isopropylsulfonyl)diazomethane, and
bis(tert-butylsulfonyl)diazomethane; glyoxime derivatives such as
bis-O-(p-toluenesulfonyl)-α-dimethylglyoxime and
bis-O-(n-butanesulfonyl)-α-dimethylglyoxime;
  bissulfone derivatives such as bisnaphthylsulfonylmethane;
  and sulfonic acid esters of N-hydroxyimide compounds such as
N-hydroxysuccinimide methanesulfonate,
N-hydroxysuccinimide trifluoromethanesulfonate,
N-hydroxysuccinimide 1-propanesulfonate,
N-hydroxysuccinimide 2-propanesulfonate,
N-hydroxysuccinimide 1-pentanesulfonate,
N-hydroxysuccinimide p-toluenesulfonate,
N-hydroxynaphthalimide methanesulfonate, and
N-hydroxynaphthalimide benzenesulfonate.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is preferably added in an amount of 0.1 to 50 parts by weight, and especially 0.5 to 40 parts by weight, per 100 parts by weight of the base resin (A). Less than 0.1 pbw of the acid generator may generate an insufficient amount of acid upon light exposure, resulting in a low sensitivity and resolution. More than 50 pbw of the acid generator may lower the transmittance of the resist and result in a poor resolution.

Component (D)

The basic compound (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of suitable basic compounds include ammonia, primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, and imide derivatives.

Examples of suitable primary aliphatic amines include methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine.

Examples of suitable secondary aliphatic amines include dimethylamine, diethylamine, di-n-propylamine, di-isopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine.

Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine.

Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, and diaminonaphthalene; and pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g., nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine).

Examples of suitable nitrogen-containing compounds having sulfonyl group include 3-pyridinesulfonic acid and pyridinium p-toluenesulfonate.

Examples of suitable nitrogen-containing compounds having hydroxyl group, nitrogen-containing compounds having hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide.

Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formula (B)-1 may also be included alone or in admixture.

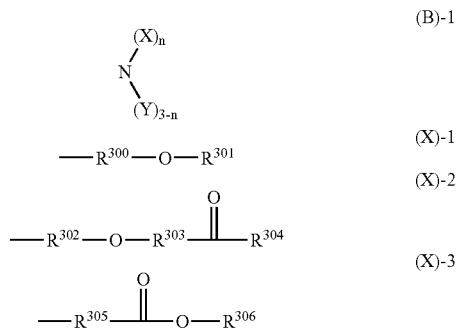

In the formulas, n is 1, 2 or 3. The side chain X may be the same or different and is represented by the formula (X)-1, (X)-2 or (X)-3. The side chain Y may be the same or different and stands for hydrogen or a straight, branched or cyclic alkyl group of 1 to 20 carbon atoms which may contain an ether or hydroxyl group. Two or three X's may bond together to form a ring. $R^{300}$, $R^{302}$ and $R^{305}$ are independently straight or branched alkylene groups of 1 to 4 carbon atoms; $R^{301}$ and $R^{304}$ are independently hydrogen or straight, branched or cyclic alkyl groups of 1 to 20 carbon atoms, which may contain at least one hydroxyl group, ether group, ester group or lactone ring; $R^{303}$ is a single bond or a straight or branched alkylene group of 1 to 4 carbon atoms; and $R^{306}$ is hydrogen or a straight, branched or cyclic alkyl group of 1 to 20 carbon atoms, which may contain at least one hydroxyl group, ether group, ester group or lactone ring.

Illustrative, non-limiting examples of the compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy) ethyl}amine, tris{2-(1-ethoxyethoxy)ethyl}amine, tris{2-(1-ethoxypropoxy)ethyl}amine, tris[2-{2-(2-hydroxyethoxy) ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl) amine, tris(2-valeryloxyethyl)amine, tris(2-pivaloyloxyethyl)amine, N,N-bis(2-acetoxyethyl)-2-(acetoxyacetoxy) ethylamine, tris(2-methoxycarbonyloxyethyl)amine, tris(2-tert-butoxycarbonyloxyethyl)amine, tris[2-(2-oxopropoxy) ethyl]amine, tris[2-(methoxycarbonylmethyl)oxyethyl] amine, tris[2-(tert-butoxycarbonylmethyloxy)ethyl]amine, tris[2-(cyclohexyloxycarbonylmethyloxy)ethyl]amine, tris (2-methoxycarbonylethyl)amine, tris(2-ethoxycarbonylethyl)amine, N,N-bis(2-hydroxyethyl)-2-(methoxycarbonyl) ethylamine, N,N-bis(2-acetoxyethyl)-2-(methoxycarbonyl) ethylamine, N,N-bis(2-hydroxyethyl)-2-(ethoxycarbonyl) ethylamine, N,N-bis(2-acetoxyethyl)-2-(ethoxycarbonyl) ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl) ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl] ethylamine, N,N-bis(2-acetoxyethyl)-2-[(2-oxotetrahydrofuran-3-yl)oxy-carbonyl]ethylamine, N,N-bis (2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl] amine, N-(2-methoxyethyl)-bis[2-(methoxycarbonyl)ethyl] amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis (methoxycarbonylmethyl)amine, and β-(diethylamino)-δ-valerolactone.

Also useful are one or more of basic compounds of cyclic structure having the following general formula (B)-2.

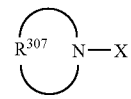

(B)-2

Herein X is a substituent group of (X)-1 to (X)-3, shown above, and $R^{307}$ is a straight or branched $C_2$-$C_{20}$ alkylene group which may contain one or more carbonyl, ether, ester or sulfide groups.

Illustrative examples of the compounds having formula (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy) methoxy]ethyl]pyrrolidine, 1-[2-[(2-methoxyethoxy)methoxy]ethyl]piperidine, 4-[2-[(2-methoxyethoxy)methoxy] ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino) propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl) propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Also, one or more of cyano-containing basic compounds having the following general formulae (B)-3 to (B)-6 may be blended.

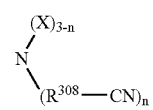

(B)-3

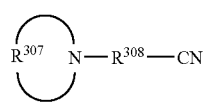

(B)-4

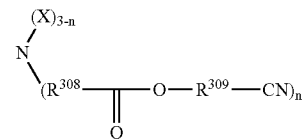

(B)-5

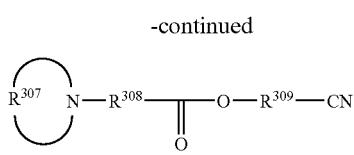

(B)-6

Herein, X is a substituent group of (X)-1 to (X)-3, shown above, $R^{307}$ is as defined above, n is 1, 2 or 3, and $R^{308}$ and $R^{309}$ each are independently a straight or branched alkylene group of 1 to 4 carbon atoms.

Illustrative examples of the basic compounds having cyano group as represented by formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiono-nitrile, N-(2-cyanoethyl)-N-(3-hydroxy-1-propyl)-3-aminopropiono-nitrile, N-(3-acetoxy-1-propyl)-N-(2-cyanoethyl)-3-aminopropiono-nitrile, N-(2-cyanoethyl)-N-(3-formyloxy-1-propyl)-3-aminopropiono-nitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl) aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-amino-propionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are basic compounds having an imidazole skeleton and a polar functional group, represented by the general formula (B)-7.

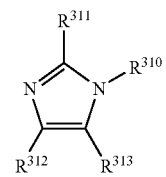

(B)-7

Herein, $R^{310}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{311}$, $R^{312}$ and $R^{313}$ are each independently a hydrogen atom, a straight, branched or cyclic alkyl group, aryl group or aralkyl group having 1 to 10 carbon atoms.

Also included are basic compounds having a benzimidazole skeleton and a polar functional group, represented by the general formula (B)-8.

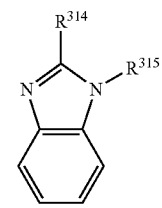

(B)-8

Herein, $R^{314}$ is a hydrogen atom, a straight, branched or cyclic alkyl group, aryl group or aralkyl group having 1 to 10 carbon atoms. $R^{315}$ is a polar functional group-bearing, straight, branched or cyclic alkyl group of 1 to 20 carbon atoms, and the alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

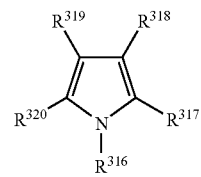

(B)-9

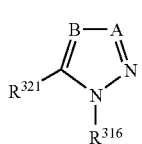
(B)-10

Herein, A is a nitrogen atom or =C—R³²², B is a nitrogen atom or =C—R³²³, R³¹⁶ is a straight, branched or cyclic alkyl group of 2 to 20 carbon atoms bearing at least one polar functional group selected from among hydroxyl, carbonyl, ester, ether, sulfide, carbonate, cyano and acetal groups; R³¹⁷, R³¹⁸, R³¹⁹ and R³²⁰ are each independently a hydrogen atom, a straight, branched or cyclic alkyl group or aryl group having 1 to 10 carbon atoms, or a pair of R³¹⁷ and R³¹⁸ and a pair of R³¹⁹ and R³²⁰, taken together, may form a benzene, naphthalene or pyridine ring with the carbon atoms to which they are attached; R³²¹ is a hydrogen atom, or a straight, branched or cyclic alkyl group or aryl group having 1 to 10 carbon atoms; R³²² and R³²³ each are a hydrogen atom, or a straight, branched or cyclic alkyl group or aryl group having 1 to 10 carbon atoms, or a pair of R³²¹ and R, taken together, may form a benzene or naphthalene ring with the carbon atoms to which they are attached.

The basic compounds or heterocyclic nitrogen-containing compounds may be used alone or in admixture of two or more. The basic compound (D) is preferably formulated in an amount of 0.001 to 2 parts, and especially 0.01 to 1 part by weight, per 100 parts by weight of the base resin (A). Less than 0.001 part of the basic compound may achieve no or little addition effect whereas more than 2 parts may result in too low a sensitivity.

Component (E)

The dissolution inhibitor (E) is a compound with a weight average molecular weight of up to 3,000 which changes its solubility in an alkaline developer under the action of an acid, and typically selected from phenol and carboxylic acid derivatives in which some or all of hydroxyl groups are substituted by acid labile groups (as described above) and which have a weight average molecular weight of up to 2,500.

Examples of the phenol or carboxylic acid derivative having a weight average molecular weight of up to 2,500 include 4,4'-(1-methylethylidene)bisphenol, (1,1'-biphenyl-4,4'-diol)-2,2'-methylenebis(4-methylphenol), 4,4-bis(4'-hydroxyphenyl)valeric acid, tris(4-hydroxyphenyl)methane, 1,1,1-tris(4'-hydroxyphenyl)ethane, 1,1,2-tris(4'-hydroxyphenyl)ethane, phenolphthalein, thimolphthalein, 3,3'-difluoro[(1,1-biphenyl)-4,4'-diol], 3,3',5,5'-tetrafluoro[(1,1'-biphenyl)-4,4'-diol], 4,4'-[2,2,2-trifluoro-1-(trifluoromethyl)ethylidene]bisphenol, 4,4'-methylenebis(2-fluorophenol), 2,2'-methylenebis(4-fluorophenol), 4,4'-isopropylidenebis(2-fluorophenol), cyclohexylidenebis(2-fluorophenol), 4,4'-[(4-fluorophenyl)methylene]bis(2-fluorophenol), 4,4'-methylenebis(2,6-difluorophenol), 4,4'-(4-fluorophenyl)methylenebis(2,6-difluorophenol), 2,6-bis[(2-hydroxy-5-fluorophenyl)methyl]-4-fluorophenol, 2,6-bis[(4-hydroxy-3-fluorophenyl)methyl]-4-fluorophenol, and 2,4-bis[(3-hydroxy-4-hydroxyphenyl)methyl]-6-methylphenol. The acid labile groups are the same as formulae (AL-1) to (AL-3) described above.

Illustrative, non-limiting, examples of the dissolution inhibitors which are useful herein include 3,3',5,5'-tetrafluoro[(1,1'-biphenyl)-4,4'-di-t-butoxycarbonyl], 4,4'-[2,2,2-trifluoro-1-(trifluoromethyl)ethylidene]-bisphenol-4,4'-di-t-butoxycarbonyl, bis(4-(2'-tetrahydropyranyloxy)phenyl)methane, bis(4-(2'-tetrahydrofuranyloxy)phenyl)methane, bis(4-tert-butoxyphenyl)methane, bis(4-tert-butoxycarbonyloxyphenyl)methane, bis(4-tert-butoxycarbonylmethyloxyphenyl)methane, bis(4-(1'-ethoxyethoxy)phenyl)methane, bis(4-(1'-ethoxypropyloxy)phenyl)methane, 2,2-bis(4'-(2''-tetrahydropyranyloxy))propane, 2,2-bis(4'-(2''-tetrahydrofuranyloxy)phenyl)propane, 2,2-bis(4'-tert-butoxyphenyl)propane, 2,2-bis(4'-tert-butoxycarbonyloxyphenyl)propane, 2,2-bis(4-tert-butoxycarbonylmethyloxyphenyl)propane, 2,2-bis(4'-(1''-ethoxyethoxy)phenyl)propane, 2,2-bis(4'-(1''-ethoxypropyloxy)phenyl)propane, tert-butyl 4,4-bis(4'-(2''-tetrahydropyranyloxy)phenyl)-valerate, tert-butyl 4,4-bis(4'-(2''-tetrahydrofuranyloxy)phenyl)-valerate, tert-butyl 4,4-bis(4'-tert-butoxyphenyl)valerate, tert-butyl 4,4-bis(4-tert-butoxycarbonyloxyphenyl)valerate, tert-butyl 4,4-bis(4'-tert-butoxycarbonylmethyloxyphenyl)-valerate, tert-butyl 4,4-bis(4'-(1''-ethoxyethoxy)phenyl)valerate, tert-butyl 4,4-bis(4'-(1''-ethoxypropyloxy)phenyl)valerate, tris(4-(2'-tetrahydropyranyloxy)phenyl)methane, tris(4-(2'-tetrahydrofuranyloxy)phenyl)methane, tris(4-tert-butoxyphenyl)methane, tris(4-tert-butoxycarbonyloxyphenyl)methane, tris(4-tert-butoxycarbonyloxymethylphenyl)methane, tris(4-(1'-ethoxyethoxy)phenyl)methane, tris(4-(1'-ethoxypropyloxy)phenyl)methane, 1,1,2-tris(4'-(2''-tetrahydropyranyloxy)phenyl)ethane, 1,1,2-tris(4'-(2''-tetrahydrofuranyloxy)phenyl)ethane, 1,1,2-tris(4'-tert-butoxyphenyl)ethane, 1,1,2-tris(4'-tert-butoxycarbonyloxyphenyl)ethane, 1,1,2-tris(4'-tert-butoxycarbonylmethyloxyphenyl)ethane, 1,1,2-tris(4'-(1'-ethoxyethoxy)phenyl)ethane, 1,1,2-tris(4'-(1'-ethoxypropyloxy)phenyl)ethane, t-butyl 2-trifluoromethylbenzenecarboxylate, t-butyl 2-trifluoromethylcyclohexanecarboxylate, t-butyl decahydronaphthalene-2,6-dicarboxylate, t-butyl cholate, t-butyl deoxycholate, t-butyl adamantanecarboxylate, t-butyl adamantaneacetate, and tetra-t-butyl 1,1'-bicyclohexyl-3,3',4,4'-tetracarboxylate.

In the resist composition of the invention, an appropriate amount of the dissolution inhibitor (E) is up to about 20 parts, and especially up to about 15 parts by weight per 100 parts by weight of the base resin (A). More than 20 parts of the dissolution inhibitor leads to resist compositions having poor heat resistance due to increased monomer contents.

In addition to the foregoing components, the resist composition of the invention may include optional ingredients, typically a surfactant which is commonly used for improving the coating characteristics. Optional ingredients may be added in conventional amounts so long as this does not compromise the objects of the invention.

A nonionic surfactant is preferred, examples of which include perfluoroalkyl polyoxyethylene ethanols, fluorinated alkyl esters, perfluoroalkylamine oxides, perfluoroalkyl EO-addition products, and fluorinated organosiloxane compounds. Illustrative examples include Fluorad FC-430 and FC-431 from Sumitomo 3M Ltd., Surflon S-141 and S-145 from Asahi Glass Co., Ltd., Unidyne DS-401, DS-403, and DS-451 from Daikin Industries Ltd., Megaface F-8151 from Dainippon Ink & Chemicals, Inc., and X-70-092 and X-70-093 from Shin-Etsu Chemical Co., Ltd. Preferred surfactants include Fluorad FC-430 from Sumitomo 3M Ltd. and X-70-093 from Shin-Etsu Chemical Co., Ltd.

Pattern formation using the resist composition of the invention may be carried out by a known lithographic technique. For example, the resist composition is applied onto a substrate such as a silicon wafer by spin coating or the like to form a resist film having a thickness of 0.1 to 1.0 µm, which is then pre-baked on a hot plate at 60 to 200° C. for 10 seconds to 10 minutes, and preferably at 80 to 150° C. for ½ to 5 minutes. A mask having the desired pattern is then placed over the resist film, and the film exposed through the mask to high-energy radiation witin a wavelength band of 100-250 nm or 1-30 nm such as deep-UV rays, excimer laser beams or x-rays, or electron beams in a dose of about 1 to 200 mJ/cm$^2$, and preferably about 10 to 100 mJ/cm$^2$, then post-exposure baked (PEB) on a hot plate at 60 to 150° C. for 10 seconds to 5 minutes, and preferably at 80 to 130° C. for ½ to 3 minutes. Finally, development is carried out using as the developer an aqueous alkali solution, such as 0.1 to 5 wt %, and preferably 2 to 3 wt %, tetramethylammonium hydroxide (TMAH), this being done by a conventional technique such as dip, puddle, or spray technique for a period of 10 seconds to 3 minutes, and preferably 30 seconds to 2 minutes. These steps result in the formation of the desired pattern on the substrate.

Of the various types of high-energy radiation that may be used, the resist composition of the invention is best suited to micro-pattern formation with, in particular, deep-UV rays having a wavelength of 254 to 120 nm, an excimer laser, especially ArF excimer laser (193 nm), F$_2$ laser (157 nm), Kr$_2$ laser (146 nm), KrAr excimer laser (134 nm) or Ar$_2$ laser (126 nm), x-rays, or electron beams. The desired pattern may not be obtainable outside the upper and lower limits of the above range.

In forming a pattern using the resist composition of the invention, another approach known as immersion lithography may be employed involving applying the resist composition by the same procedure as described above, feeding a liquid between the wafer and a projection lens, and exposing the resist coating to high-energy radiation through a mask. The liquid fill between the wafer and the projection lens should have a high refractive index and high transparency. In the ArF immersion lithography, water having a refractive index of 1.44 at wavelength 193 nm is often used.

In the practice of immersion lithography, a protective film may be formed on the resist film prior to light exposure, in order to prevent the acid generated and the basic compound added to the resist film from being dissolved in water. The protective film is formed by using any well-known polymer as the protective coating material, dissolving it in a solvent, and applying the solution onto the resist film by a suitable technique such as spin coating. The protective film preferably has a thickness of 10 to 500 nm. Light exposure is carried out by inserting a liquid between the resist protective film and the projection lens and irradiating high-energy radiation to the resist film through the projection lens and the mask.

The protective film is then stripped by a technique which is selected in accordance with the identity of the protective coating material. In the case of alkali-soluble protective coating material, the protective film is stripped at the same time as the resist film is developed with an alkaline developer liquid. In the case of alkali-insoluble protective coating material, the protective film is removed using a stripper liquid prior to development.

EXAMPLE

Examples of the invention are given below by way of illustration and not by way of limitation. The weight average molecular weight (Mw) and number average molecular weight (Mn) are determined by gel permeation chromatography (GPC) versus polystyrene standards.

Monomer Synthesis Example 1

Synthesis of Monomer 1

In a nitrogen stream, a 200-mL flask was charged with 16.9 g of alcohol reactant 1, shown below, and 50 g of methylene chloride and cooled in an ice bath. Then 10.2 g of (α-trifluoromethyl)acrylic chloride was added dropwise from a dropping funnel to the flask over 5 minutes. Then 6.0 g of triethylamine was added dropwise from a dropping funnel to the flask over 15 minutes. After triethylamine had been added in entirety, the flask was kept in the ice bath for reaction to occur for 2 hours. Water, 100 g, was added to the reaction system, and the organic layer was washed with a saturated sodium hydrogen carbonate solution. Thereafter, the organic layer was washed twice with 100 g of water and dried over sodium sulfate. The sodium sulfate was separated off, the solution was concentrated under reduced pressure in an evaporator. Hexane was added to the remaining oily matter. Subsequent cooling yielded a white crystalline solid, which is designated Monomer 1. The amount was 18.2 g and the yield was 69.4%.

FT-IR (KBr): ν=2973, 2942, 2925, 2877, 1791, 1731, 1720, 1461, 1409, 1384, 1346, 1305, 1295, 1247, 1211, 1178, 1155, 1137, 1116, 1110, 1058, 1043, 1010, 983, 948, 933, 809, 746, 700 cm$^{-1}$ $^1$H-NMR (300.5 MHz in DMSO-d6): δ=0.82 (t, J=7.3 Hz, 3H), 1.55-2.01 (m, 12H), 2.70-3.32 (m, 4H), 4.55-4.77 (m, 2H), 4.82 (s, 1H), 6.77 (m, 1H), 6.93 (m, 1H) ppm $^{13}$C-NMR (75.6 MHz in CHCl$_3$-dl): δ=8.8, 24.0, 29.6, 31.9, 37.1, 41.5, 44.6, 45.5, 48.2, 79.4, 83.8, 95.7, 126.5, 130.3, 134.3, 159.9, 169.6, 177.6 ppm $^{19}$F-NMR (282.8 MHz in DMSO-d6): δ=−65.4 (total: 3F) ppm

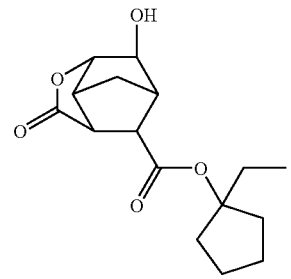

Alcohol 1

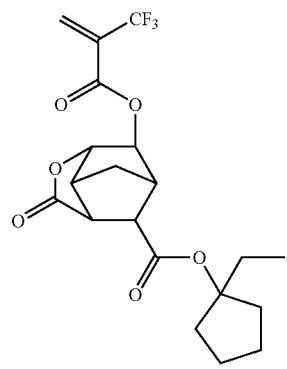

Monomer 1

Polymer Synthesis Example 1

Synthesis of Polymer 1

A 200-ml flask was charged with 15.60 g of Monomer 1, 4.40 g of Monomer 2, shown below, and 8.58 g of toluene as a solvent. In a nitrogen atmosphere, the reactor was cooled to −70° C., followed by vacuum evacuation and nitrogen flow, which were repeated three times. The reactor was warmed up to room temperature, 0.26 g of AIBN as a polymerization initiator was added, and the reactor was heated to 60° C., whereupon reaction occurred for 24 hours. The reaction solution was poured into 300 g of n-hexane for precipitation. The resulting polymer was washed with n-hexane, separated and vacuum dried at 40° C. for 20 hours. This polymer is designated Polymer 1.

The polymer was analyzed for composition by $^1$H-NMR and for molecular weight by GPC, with the results being shown below. The yield was 72.5%.

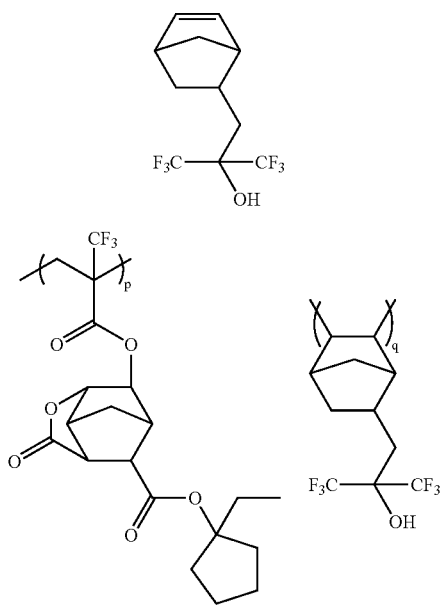

Mw = 9,800, Mw/Mn = 1.5, p:q = 69:31

Polymer Synthesis Example 2

Synthesis of Polymer 2

A 200-ml flask was charged with 4.01 g of Monomer 2, 16.00 g of Monomer 3, shown below, and 8.58 g of toluene as a solvent. In a nitrogen atmosphere, the reactor was cooled to −70° C., followed by vacuum evacuation and nitrogen flow, which were repeated three times. The reactor was warmed up to room temperature, 0.24 g of AIBN as a polymerization initiator was added, and the reactor was heated to 60° C., whereupon reaction occurred for 24 hours. The reaction solution was poured into 300 g of n-hexane for precipitation. The resulting polymer was washed with n-hexane, separated and vacuum dried at 40° C. for 20 hours. This polymer is designated Polymer 2.

The polymer was analyzed for composition by $^1$H-NMR and for molecular weight by GPC, with the results being shown below. The yield was 70.3%.

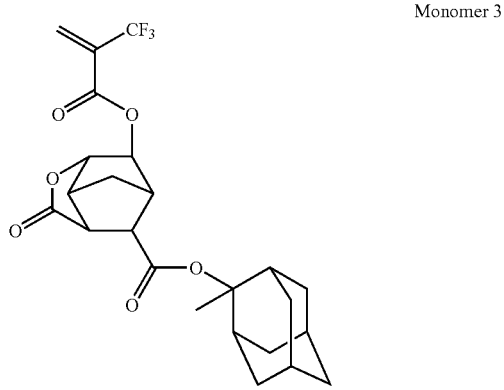

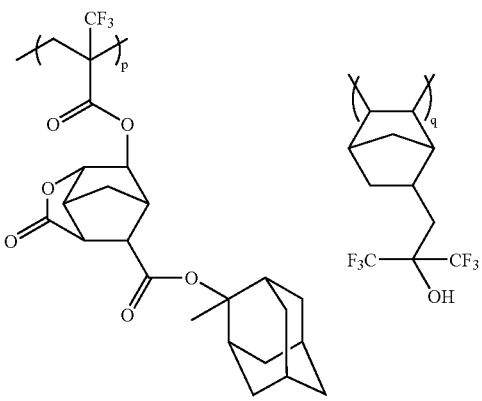

Mw = 9,200, Mw/Mn = 1.5, p:q = 66:34

Polymer Synthesis Example 3

Synthesis of Polymer 3

A 200-ml flask was charged with 3.92 g of Monomer 2, 16.08 g of Monomer 4, shown below, and 8.58 g of toluene as a solvent. In a nitrogen atmosphere, the reactor was cooled to −70° C., followed by vacuum evacuation and nitrogen flow, which were repeated three times. The reactor was warmed up to room temperature, 0.24 g of AIBN as a polymerization initiator was added, and the reactor was heated to 60° C., whereupon reaction occurred for 24 hours. The reaction solution was poured into 300 g of n-hexane for precipitation. The resulting polymer was washed with n-hexane, separated and vacuum dried at 40° C. for 20 hours. This polymer is designated Polymer 3.

The polymer was analyzed for composition by $^1$H-NMR and for molecular weight by GPC, with the results being shown below. The yield was 72.5%.

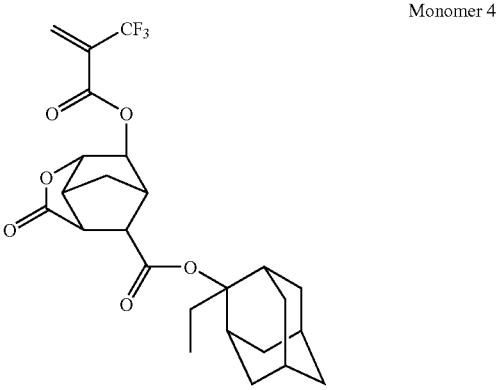

-continued

Polymer 3

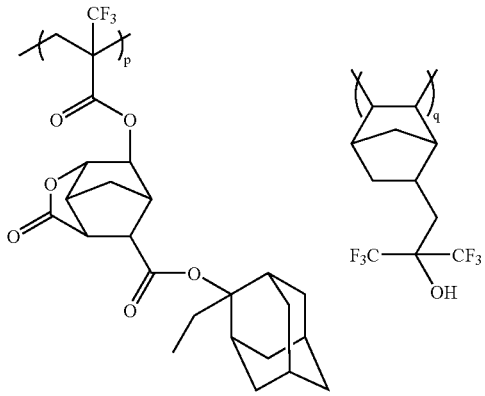

Mw = 10,500, Mw/Mn = 1.5, p:q = 67:33

Polymer Synthesis Example 4

Synthesis of Polymer 4

A 200-ml flask was charged with 9.38 g of Monomer 1, 5.30 g of Monomer 2, 5.32 g of Monomer 5, shown below, and 8.58 g of toluene as a solvent. In a nitrogen atmosphere, the reactor was cooled to −70° C., followed by vacuum evacuation and nitrogen flow, which were repeated three times. The reactor was warmed up to room temperature, 0.32 g of AIBN as a polymerization initiator was added, and the reactor was heated to 60° C., whereupon reaction occurred for 24 hours. The reaction solution was poured into 300 g of n-hexane for precipitation. The resulting polymer was washed with n-hexane, separated and vacuum dried at 40° C. for 20 hours. This polymer is designated Polymer 4.

The polymer was analyzed for composition by $^1$H-NMR and for molecular weight by GPC, with the results being shown below. The yield was 74.1%.

Monomer 5

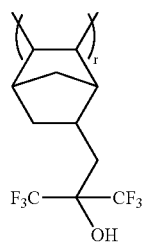

Polymer 4

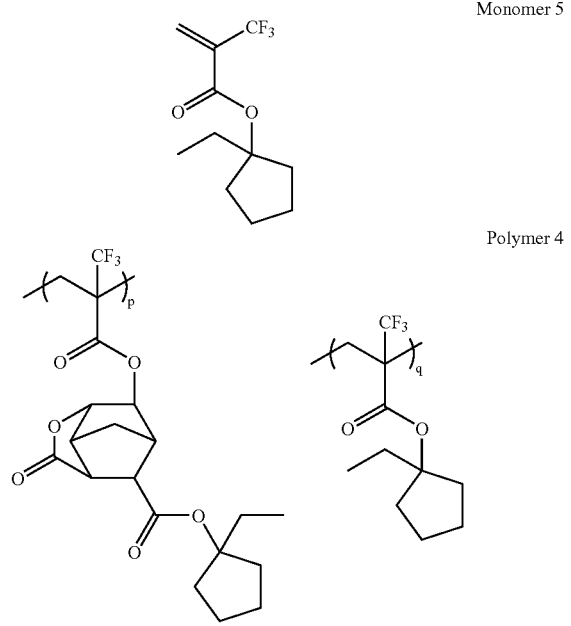

-continued

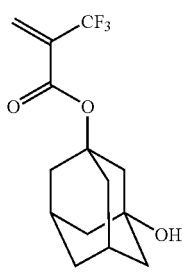

Mw = 9,400, Mw/Mn = 1.5, p:q:r = 34:36:30

Polymer Synthesis Example 5

Synthesis of Polymer 5

A 200-ml flask was charged with 12.33 g of Monomer 1, 4.87 g of Monomer 2, 2.80 g of Monomer 6, shown below, and 8.58 g of toluene as a solvent. In a nitrogen atmosphere, the reactor was cooled to −70° C., followed by vacuum evacuation and nitrogen flow, which were repeated three times. The reactor was warmed up to room temperature, 0.29 g of AIBN as a polymerization initiator was added, and the reactor was heated to 60° C., whereupon reaction occurred for 24 hours. The reaction solution was poured into 300 g of n-hexane for precipitation. The resulting polymer was washed with n-hexane, separated and vacuum dried at 40° C. for 20 hours. This polymer is designated Polymer 5.

The polymer was analyzed for composition by $^1$H-NMR and for molecular weight by GPC, with the results being shown below. The yield was 70.0%.

Monomer 6

Polymer 5

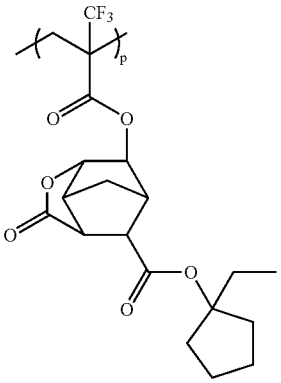

-continued

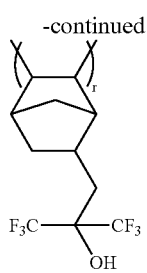

Mw = 9,200, Mw/Mn = 1.5, p:q:r = 51:19:30

Polymer Synthesis Example 6

Synthesis of Polymer 6

A 200-ml flask was charged with 13.67 g of Monomer 1, 3.10 g of Monomer 6, 3.23 g of Monomer 7, shown below, and 8.58 g of toluene as a solvent. In a nitrogen atmosphere, the reactor was cooled to −70° C., followed by vacuum evacuation and nitrogen flow, which were repeated three times. The reactor was warmed up to room temperature, 0.32 g of AIBN as a polymerization initiator was added, and the reactor was heated to 60° C., whereupon reaction occurred for 24 hours. The reaction solution was poured into 300 g of n-hexane for precipitation. The resulting polymer was washed with n-hexane, separated and vacuum dried at 40° C. for 20 hours. This polymer is designated Polymer 6.

The polymer was analyzed for composition by $^1$H-NMR and for molecular weight by GPC, with the results being shown below. The yield was 66.8%.

Monomer 7

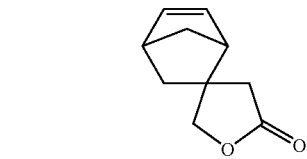

Polymer 6

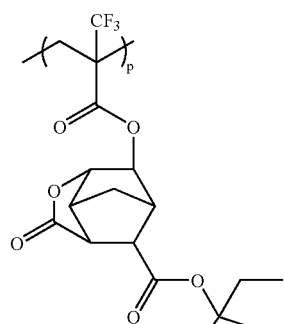

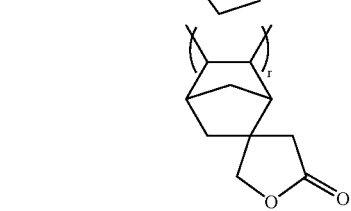

Mw = 9,600, Mw/Mn = 1.5, p:q:r = 49:19:32

Comparative Synthesis Example 1

Synthesis of Comparative Polymer 1

A 300-ml flask was charged with 8.37 g of Monomer A, 5.97 g of Monomer B, 5.66 g of Monomer C, all shown below, and 60.0 g of toluene as a solvent. In a nitrogen atmosphere, the reactor was cooled to −70° C., followed by vacuum evacuation and nitrogen flow, which were repeated three times. The reactor was warmed up to room temperature, 0.42 g of AIBN as a polymerization initiator was added, and the reactor was heated to 60° C., whereupon reaction occurred for 24 hours. The reaction solution was poured into 400 g of n-hexane for precipitation. The resulting polymer was washed with n-hexane, separated and vacuum dried at 40° C. for 20 hours. This polymer is designated Comparative Polymer 1.

The polymer was analyzed for composition by $^1$H-NMR and for molecular weight by GPC, with the results being shown below. The yield was 89.8%.

Monomer A

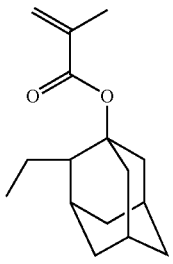

Mol. Wt.: 248.36

Monomer B

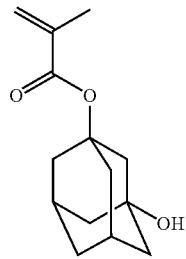

Mol. Wt.: 236.31

Monomer C

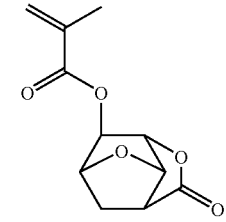

Mol. Wt.: 224.21

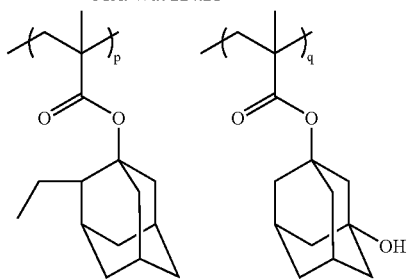

-continued

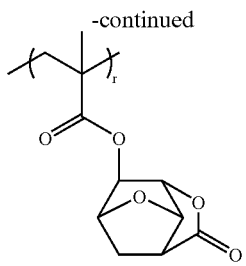

Mw = 7,700, Mw/Mn = 1.7, p:q:r = 40:30:30

Resist Preparation and Exposure

Resist solutions were prepared by mixing the polymer (Polymers 1 to 6, or Comparative Polymer 1), photoacid generator (PAG1 to PAG3), basic compound (TMMEA, AAA, or AACN) and dissolution inhibitor (DRI1) in a solvent (PGMEA) in the amounts shown in Table 1 and processing in an ordinary manner.

On silicon wafers having a film of ARC-29A (Nissan Chemicals Industries, Ltd.) coated to a thickness of 78 nm, the resist solutions were spin coated, then baked on a hot plate at 110° C. for 90 seconds to give resist films having a thickness of 200 nm.

The resist films were exposed by means of an ArF excimer laser scanner model NSR-S307E (Nikon Corp., NA 0.85, σ 0.93, 6% halftone phase shift mask, +30 nm bias, 120 nm hole, 240 nm pitch) while varying the exposure dose and focus. Immediately after exposure, the resist films were baked (PEB) at 120° C. for 60 seconds and then developed for 60 seconds with a 2.38 wt % aqueous solution of tetramethylammonium hydroxide, obtaining positive patterns.

The resist patterns were evaluated. The exposure dose (mJ/cm$^2$) at which the 120-nm hole pattern was kept open in the range of 115-125 nm is the optimum dose Eop. The focus margin (DOF) at which holes were open at a size equal to or greater than 100 nm was determined. The results are also shown in Table 1.

TABLE 1

| Polymer (pbw) | Photoacid generator (pbw) | Basic compound (pbw) | Dissolution inhibitor (pbw) | Solvent (pbw) | Sensitivity (mJ/cm$^2$) | DOF (μm) |
|---|---|---|---|---|---|---|
| Polymer 1 (100) | PAG1 (3.0) | TMMEA (0.3) | — | PGMEA (800) | 35 | 0.6 |
| Polymer 2 (100) | PAG1 (3.0) | TMMEA (0.3) | — | PGMEA (800) | 44 | 0.5 |
| Polymer 3 (100) | PAG1 (3.0) | TMMEA (0.3) | — | PGMEA (800) | 41 | 0.5 |
| Polymer 4 (100) | PAG1 (3.0) | TMMEA (0.3) | — | PGMEA (800) | 38 | 0.7 |
| Polymer 5 (100) | PAG1 (3.0) | TMMEA (0.3) | — | PGMEA (800) | 43 | 0.5 |
| Polymer 6 (100) | PAG1 (3.0) | TMMEA (0.3) | — | PGMEA (800) | 44 | 0.5 |
| Polymer 4 (100) | PAG2 (4) PAG3 (3) | TMMEA (0.3) | — | PGMEA (800) | 48 | 0.6 |
| Polymer 4 (100) | PAG1 (3.0) | AAA (0.3) | — | PGMEA (800) | 44 | 0.7 |
| Polymer 4 (100) | PAG1 (3.0) | AACN (0.3) | — | PGMEA (800) | 47 | 0.7 |
| Polymer 4 (100) | PAG1 (3.0) | TMMEA (0.3) | DRI1 (10) | PGMEA (800) | 30 | 0.6 |
| Comparative Polymer 1 (100) | PAG1 (3.0) | TMMEA (0.3) | — | PGMEA (800) | 48 | 0.3 |

PGMEA: propylene glycol monomethyl ether acetate

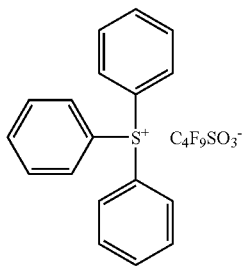

PAG1

-continued

PAG2
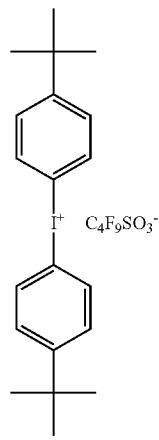

PAG3
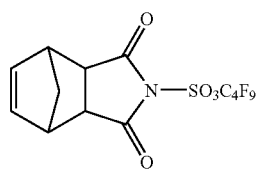

DRI1
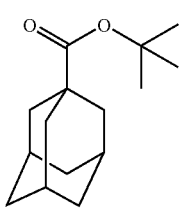

TMMEA
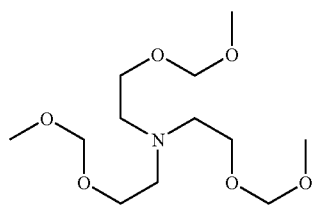

AAA
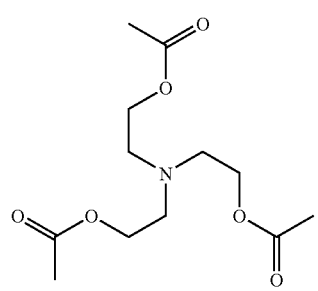

AACN
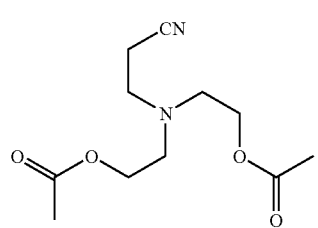

Dry Etching Test

Each polymer, 2 g, was thoroughly dissolved in 10 g of PGMEA and passed through a filter having a pore size of 0.2 µm, obtaining a polymer solution. The polymer solution was spin coated onto a silicon substrate and baked, forming a polymer film of 300 nm thick. Dry etching tests were carried out on the polymer films by etching them under two sets of conditions. In an etching test with $CHF_3/CF_4$ gas, a dry etching instrument TE-8500P (Tokyo Electron Ltd.) was used. In an etching test with $Cl_2/BCl_3$ gas, a dry etching instrument L-507D-L (Nichiden Anelva Corp.) was used. In each test, the difference in polymer film thickness before and after etching was determined. The etching conditions are summarized in Table 2.

TABLE 2

|  | $CHF_3/CF_4$ gas | $Cl_2/BCl_3$ gas |
|---|---|---|
| Chamber pressure (Pa) | 40.0 | 40.0 |
| RF power (W) | 1000 | 300 |
| Gap (mm) | 9 | 9 |
| Gas flow rate (ml/min) | $CHF_3$: 30 | $Cl_2$: 30 |
|  | $CF_4$: 30 | $BCl_3$: 30 |
|  | Ar: 100 | $CHF_3$: 100 |
|  |  | $O_2$: 2 |
| Time (sec) | 60 | 60 |

The results of etching tests are shown in Table 3. In this evaluation, a less difference in polymer film thickness, i.e., a less film loss indicates more etching resistance. It is seen that inventive resist compositions have etching resistance-comparable to the prior art resist compositions.

TABLE 3

| Polymer | $CHF_3/CF_4$ gas etching rate (nm/min) | $Cl_2/BCl_3$ gas etching rate (nm/min) |
|---|---|---|
| Polymer 1 | 130 | 150 |
| Polymer 2 | 125 | 140 |
| Polymer 3 | 122 | 139 |
| Polymer 4 | 126 | 144 |
| Polymer 5 | 122 | 138 |
| Polymer 6 | 122 | 140 |
| Comparative Polymer 1 | 144 | 168 |

Japanese Patent Application No. 2005-349110 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer comprising recurring units having the general formula (2), recurring units having the general formula (3) and recurring units having the general formula (4), the polymer having a weight average molecular weight of 1,000 to 500,00,

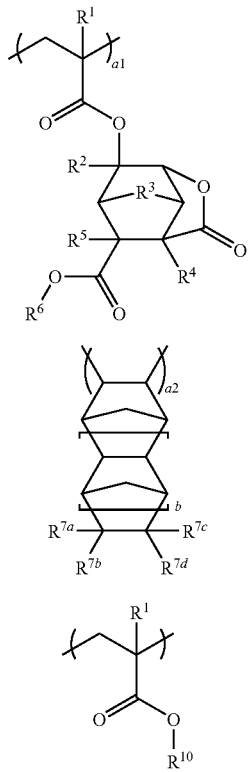

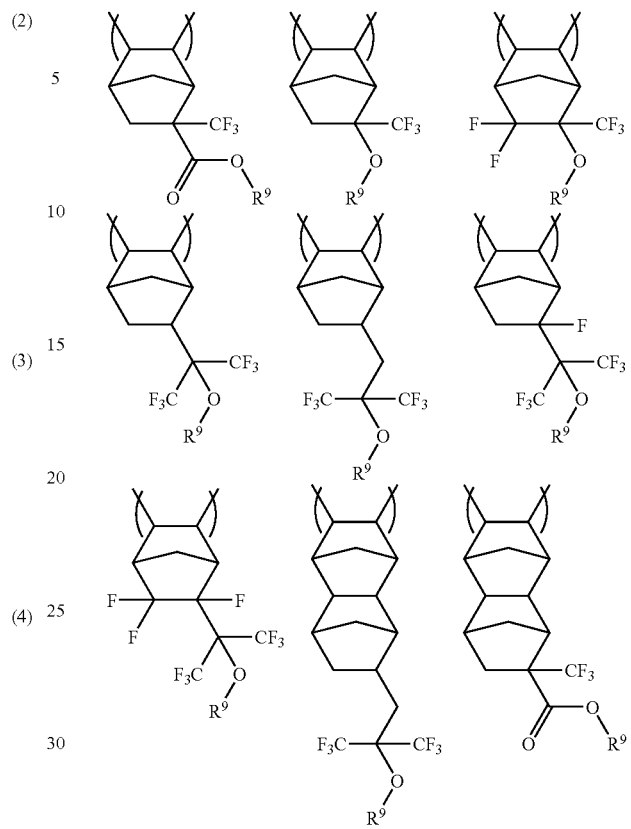

wherein $R^1$ is a fluorine atom or a straight or branched fluorinated alkyl group of 1 to 6 carbon atoms, $R^2$ is a hydrogen atom or a straight, branched or cyclic alkyl group of 1 to 8 carbon atoms, $R^3$ is an oxygen atom or a straight, branched or cyclic alkylene group of 1 to 6 carbon atoms, $R^4$ and $R^5$ each are a hydrogen atom or a straight, branched or cyclic alkyl or fluorinated alkyl group of 1 to 10 carbon atoms, $R^6$ is a hydrogen atom or an acid labile group, $R^{10}$ is a hydrogen atom, a straight, branched or cyclic fluorinated alkyl group of 1 to 10 carbon atoms, an acid labile group, or an adhesive group, the subscripts a1 and a2 are 0<a1<1, 0<a2<1, and 0<a1+a2≦1 and the subscript b is 0 or 1, said recurring units (3) are selected from the group consisting of the following units:

wherein $R^9$ is hydrogen or an acid labile group.

2. A resist composition comprising the polymer of claim 1.

3. A chemically amplified positive resist composition comprising (A) the polymer of claim 1, (B) an organic solvent, and (C) a photoacid generator.

4. A process for forming a pattern, comprising the steps of (1) applying the resist composition of claim 2 onto a substrate to form a coating, (2) heat treating the coating and exposing it to high-energy radiation in a wavelength band of 100 to 250 nm or 1 to 30 nm through a photomask, and (3) optionally heat treating and developing the exposed coating with a developer.

\* \* \* \* \*